(12) United States Patent
Schryver

(10) Patent No.: US 11,813,614 B2
(45) Date of Patent: *Nov. 14, 2023

(54) CRYOGENIC SYSTEMS

(71) Applicant: BioLife Solutions, Inc., Bothell, WA (US)

(72) Inventor: Brian Schryver, Redwood City, CA (US)

(73) Assignee: BIOLIFE SOLUTIONS, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,102

(22) Filed: Dec. 9, 2021

(65) Prior Publication Data
US 2022/0323962 A1 Oct. 13, 2022

Related U.S. Application Data

(63) Continuation of application No. 16/427,613, filed on May 31, 2019, now Pat. No. 11,229,913, which is a continuation of application No. 14/895,484, filed as application No. PCT/US2014/040756 on Jun. 3, 2014, now Pat. No. 10,307,761.

(60) Provisional application No. 61/928,367, filed on Jan. 16, 2014, provisional application No. 61/890,036, filed on Oct. 11, 2013, provisional application No. 61/879,624, filed on Sep. 18, 2013, provisional application No. 61/873,298, filed on Sep. 3, 2013, provisional application No. 61/860,801, filed on Jul. 31, 2013, provisional application No. 61/830,354, filed on Jun. 3, 2013.

(51) Int. Cl.
*B01L 7/00* (2006.01)
*B01L 7/04* (2010.01)
*C12M 1/00* (2006.01)
*F25D 3/12* (2006.01)

(52) U.S. Cl.
CPC .................. *B01L 7/50* (2013.01); *B01L 7/04* (2013.01); *C12M 45/22* (2013.01); *F25D 3/125* (2013.01); *B01L 2200/025* (2013.01); *B01L 2200/143* (2013.01); *B01L 2300/025* (2013.01); *B01L 2300/0854* (2013.01); *B01L 2300/1894* (2013.01)

(58) Field of Classification Search
CPC ..... B01L 2300/1894; B01L 2300/0854; B01L 2300/025; B01L 7/04; F25D 3/125; C12M 45/22

See application file for complete search history.

(56) References Cited

U.S. PATENT DOCUMENTS

| | | | |
|---|---|---|---|
| 2,608,838 A | 9/1952 | Rupp | |
| 3,108,840 A | 10/1963 | Conrad et al. | |
| 3,257,820 A | 6/1966 | Case et al. | |
| 3,864,936 A | 2/1975 | Frank et al. | |
| 3,971,231 A | 7/1976 | Derry | |

(Continued)

FOREIGN PATENT DOCUMENTS

| | | |
|---|---|---|
| CN | 105492819 A | 4/2016 |
| GB | 1518792 A | 7/1978 |

(Continued)

*Primary Examiner* — Ana M Vazquez
(74) *Attorney, Agent, or Firm* — Brown & Michaels, PC

(57) ABSTRACT

Cryogenic devices are provided in which solid carbon dioxide (dry ice) is used to maintain a temperature zone in which samples can be manipulated under conditions in which the sample is maintained at a temperature below −50° C.

22 Claims, 28 Drawing Sheets

(56) References Cited

U.S. PATENT DOCUMENTS

| | | |
|---|---|---|
| 4,494,415 A | 1/1985 | Elliston |
| 4,741,167 A | 5/1988 | Wigley |
| 4,875,340 A | 10/1989 | Liu et al. |
| 5,048,300 A | 9/1991 | Lihl |
| 5,080,935 A | 1/1992 | Kelso, Jr. et al. |
| 5,309,722 A | 5/1994 | Phillips, Jr. |
| 5,410,910 A | 5/1995 | Yang et al. |
| 5,475,981 A | 12/1995 | Becker |
| 5,606,860 A | 3/1997 | Popp et al. |
| 5,671,603 A | 9/1997 | McCorkle et al. |
| 5,924,302 A | 7/1999 | Derifield |
| 6,065,303 A | 5/2000 | Harris |
| 6,122,232 A | 9/2000 | Schell et al. |
| 6,212,901 B1 | 4/2001 | Pint et al. |
| 6,266,306 B1 | 7/2001 | Schell et al. |
| 6,295,830 B1 | 10/2001 | Newman |
| 8,191,380 B2 | 6/2012 | Aragon |
| 10,307,761 B2 | 6/2019 | Schryver |
| 2002/0050147 A1 | 5/2002 | Mai et al. |
| 2005/0006272 A1 | 1/2005 | Derifield |
| 2005/0016198 A1 | 1/2005 | Wowk et al. |
| 2005/0039484 A1 | 2/2005 | Nielsen |
| 2005/0157774 A1 | 7/2005 | DiLuiso et al. |
| 2005/0178770 A1 | 8/2005 | Hase et al. |
| 2005/0188715 A1 | 9/2005 | Aragon |
| 2006/0076385 A1 | 4/2006 | Etter et al. |
| 2006/0218963 A1 | 10/2006 | Elias |
| 2006/0283197 A1 | 12/2006 | Schon et al. |
| 2007/0084232 A1 | 4/2007 | Whewell |
| 2007/0151283 A1 | 7/2007 | Whewell |
| 2008/0292220 A1 | 11/2008 | Zacchi |
| 2008/0302119 A1 | 12/2008 | Shaw |
| 2009/0230139 A1 | 9/2009 | Li |
| 2011/0064605 A1 | 3/2011 | Hedman |
| 2012/0098434 A1 | 4/2012 | Sondericker, III |
| 2012/0102983 A1 | 5/2012 | Parmegiani |
| 2012/0140413 A1 | 6/2012 | Rawson et al. |
| 2012/0255313 A1 | 10/2012 | Katkov et al. |
| 2012/0279896 A1 | 11/2012 | Lantz |
| 2014/0033759 A1 | 2/2014 | Ide et al. |
| 2014/0047851 A1 | 2/2014 | Zhou et al. |
| 2016/0114326 A1 | 4/2016 | Schryver |
| 2016/0143270 A1 | 5/2016 | Schryver |

FOREIGN PATENT DOCUMENTS

| | | |
|---|---|---|
| JP | 1281383 A2 | 11/1989 |
| JP | 2001024243 A | 1/2001 |
| JP | 2005021978 A | 1/2005 |
| WO | 2012112035 A1 | 8/2012 |
| WO | 2014197511 A2 | 12/2014 |
| WO | 2014197515 A1 | 12/2014 |

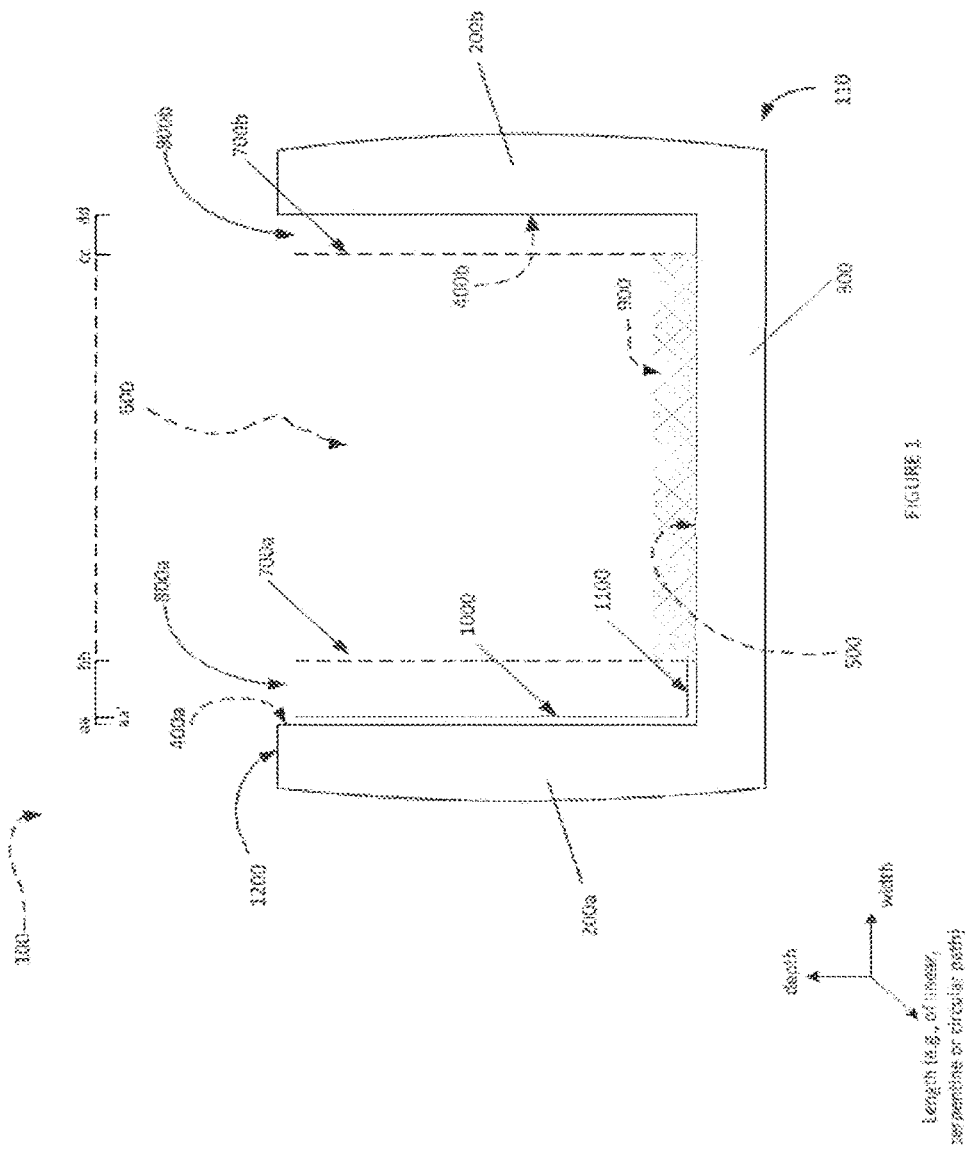

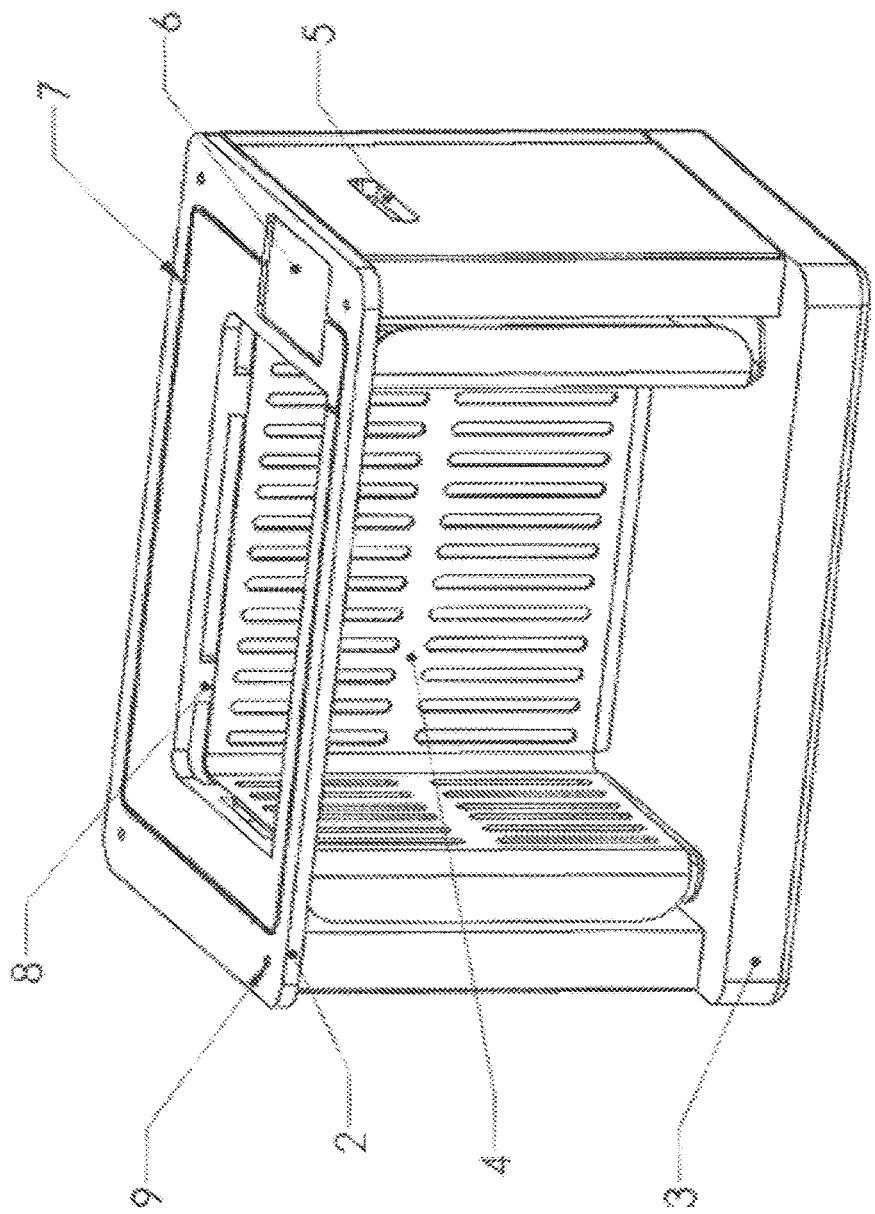

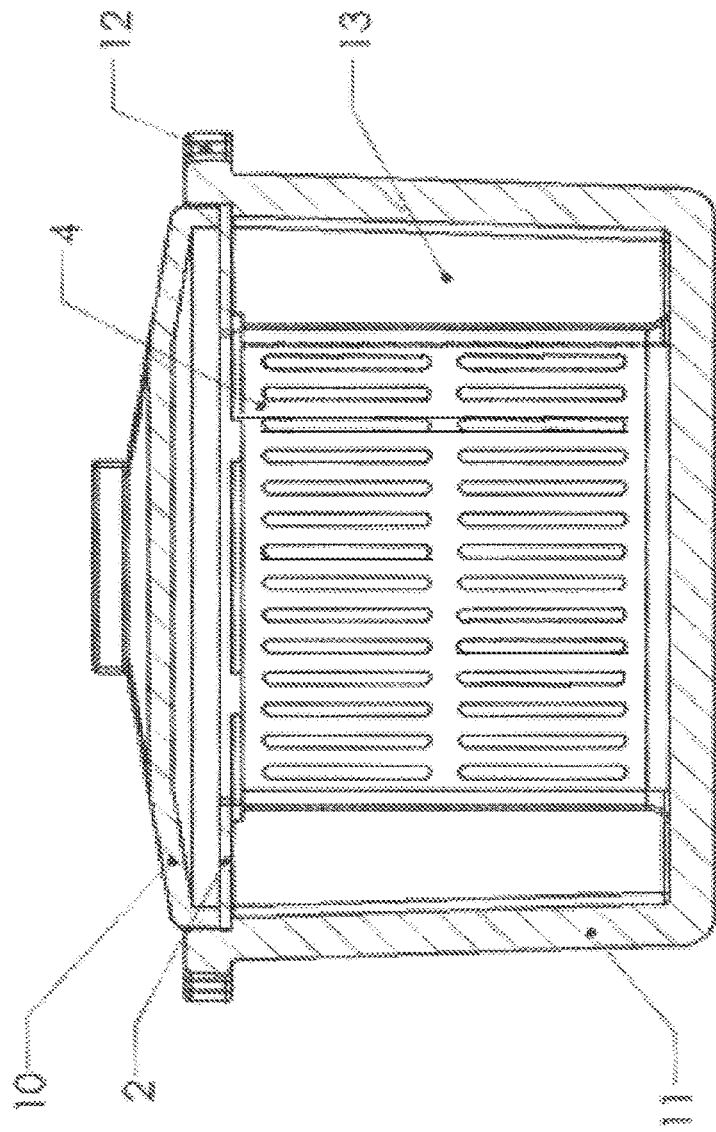

CRYOGENIC SYSTEMS

CROSS-REFERENCES TO RELATED APPLICATIONS

This application is a continuation of U.S. patent application Ser. No. 16/427,613, filed May 31, 2019, which is a continuation of U.S. patent application Ser. No. 14/895,484, filed Dec. 2, 2015, which is a U.S. National Phase Patent application of PCT Application No. PCT/US2014/040756 filed on Jun. 3, 2014, which claims benefit of each of the following provisional applications: No. 61/830,354 (filed Jun. 3, 2013); No. 61/860,801 (filed Jul. 31, 2013); No. 61/873,298 (filed Sep. 3, 2013); No. 61/879,624 (filed Sep. 18, 2013); No. 61/890,036 (filed Oct. 11, 2013); and No. 61/928,367 (filed Jan. 16, 2014). The entire contents of each of these applications is incorporated herein by reference for all purposes.

FIELD OF THE INVENTION

The invention relates to systems for maintaining samples at ultra-low temperatures.

BACKGROUND OF THE INVENTION

Many industrial, commercial, and research processes require, for optimal results, that an object or material be maintained at a low temperature. For example, cryogenic preservation or maintenance at low temperature is a common means of insuring the molecular integrity of specimens and products. Substances that would degrade in a relatively short interval at higher temperatures can be stored with limited or no change for long durations at temperatures below the material freezing point. While frozen storage can be effective in decreasing the rate of sample degradation, in aqueous solutions and biological specimens, molecular activity does not cease until a temperature near −130° C. At temperatures above this point, there remains an opportunity for the specimen to re-order the solid structure, thereby creating changes in the specimen that may lead to a decrease in the integrity of the sample. Examples of this type of sample damage include, upon thawing, a decrease in viability of cryogenically stored cells, a reduction of enzymatic activity, and a decrease in the potency of pharmaceuticals.

The opportunity for deleterious changes in frozen specimens increases greatly under conditions where the sample experiences transient fluctuations in temperature such as may occur when stored materials are transferred from one cold storage system to another, or when held inside a storage system that undergoes temperature spikes, such as those introduced when a freezer door is opened for normal access, during intervals of power failure, or even during normal mechanical refrigeration temperature cycles over time.

Despite the need for prevention of temperature spikes and fluctuations in samples, there is often a need for extensive manipulation of samples outside of the normal frozen storage system. For example, cell vials may need to be re-organized, cataloged, or traced, requiring exposure to higher temperatures for time periods of several minutes to one-half of an hour or longer. Other requirements for extended manipulation time outside of freezer storage include preparation of samples for shipping or local transport; receiving, sorting, and storage of sample shipments; and packaging and labeling of frozen products.

BRIEF SUMMARY OF THE INVENTION

In one aspect a system for cryogenic processing is provided. In one aspect the system comprises: (a) a container comprising an insulated chamber, said chamber comprising i) a chamber floor, ii) at least one chamber wall, iii) a chamber opening above the chamber floor, said opening suitable for introduction of samples into the chamber; and (b) at least one gas permeable dry-ice retainer vertically disposed within the chamber and positioned to permit direct access to the chamber floor through the chamber opening, wherein the retainer(s) divides the chamber into i) a sample-holding portion comprising at least part of the chamber floor, and ii) at least one dry ice retention space. In some embodiments, the total volume of the dry ice retention space(s) is less than the volume of the sample-holding portion. In some embodiments, following an equilibration period, filling the dry ice retention space(s) with dry ice results in a chamber temperature below −50° C. for at least four hours as measured 1 inch above the chamber floor in the sample-holding portion of the chamber, without requiring the addition of more dry ice to the dry ice retention space(s), when said container is located within a 25° C. room with the chamber opening being constantly open for user access during said four hours. In one aspect the system for cryogenic processing comprises i) a container comprising one or more sides and a floor forming an interior chamber with an open top, and ii) a retainer positioned in close proximity to an interior side wall, wherein said retainer is capable of holding dry ice pieces and exhausting $CO_2$ gas directly into the interior chamber.

In certain embodiments of the system, the chamber opening comprises a collar that extends partially or completely over at least one dry ice retention space. In certain embodiments the system comprises a cover. In certain embodiments the chamber shape is (i) a rectangular prism or (ii) annular. In certain embodiments of the system the container is formed from modular components. In certain embodiments of the system the container comprises a material with a thermal conductivity less than 0.2 watts per meter kelvin.

In certain embodiments of the system, the number of dry ice retainers is greater than 1. In certain embodiments of the system the dry ice retainer is mounted on or in close proximity to a chamber wall.

In certain embodiments of the system, at least one dry ice retention space is disposed between a dry ice retainer element and a chamber wall. In certain embodiments of the system at least one dry ice retention space is a free-standing column.

In certain embodiments of the system, the retainer comprises peripheral structures, such as flanges. In some embodiments the flanges are constructed to position the retainer relative to a chamber wall. In some embodiments the flanges are constructed to confine dry ice in the dry ice retention space.

In certain embodiments of the system, the dry ice retainer is constructed from aluminium and comprises slots that render the retainer gas permeable. In certain embodiments the retainer is removable. In certain embodiments of the system the chamber is constructed to accept a plurality of different retainers with different properties. In certain embodiments of the system the chamber volume is at least 6 times the volume of the total volume of the dry ice retainer(s).

In certain embodiments, the system comprises a temperature sensor in the chamber positioned at a height above the chamber floor, wherein said sensor is suitable for measuring gas temperatures at least in the range −70° C. to −50° C., and optionally wherein the temperature sensor is a thermocouple or an RTD sensor. The system may have multiple temperature sensors positioned at the same or different heights above the chamber floor. In certain embodiments the system comprises a microprocessor receiving electric signals from one or more temperature sensors, and delivering an electric signal to an alarm system if the temperature exceeds a pre-set limit.

In certain embodiments, the system comprises an indicator marking a boundary at a specified height above the chamber floor. In certain embodiments the system comprises an indicator means for marking a boundary at a specified height above the chamber floor, such as a laser for projecting light along a horizontal path at the same level as the sensor. The horizontal path may mark the upper boundary of the low temperature zone.

In certain embodiments the system comprises a harness mounted on a retainer, said harness having affixed thereto one or more temperature sensors and/or one of more laser diodes.

In an aspect of the invention a system is provided in which the dry ice retention space(s) contain dry ice pieces. In an aspect, the sample-holding portion of the chamber is substantially free of dry ice pieces.

In one aspect the invention provides a method of manipulating a sample under cryogenic conditions comprising manipulating the sample in the low temperature zone of a system described herein for cryogenic processing.

In one aspect the invention provides a method of making a cryogenic system by inserting at least one retainer into an insulated chamber of a container, wherein the retainer comprises a gas permeable dry-ice retainer element and the retainer is positioned in the chamber to create at least one dry ice retention space and a sample-holding space, wherein the total volume of the dry ice retention space(s) is less than the volume of the sample-holding portion.

In one aspect the invention provides a method of charging a cryogenic processing system by introducing a plurality of pieces of dry ice into the dry ice retention space(s) of the cryogenic processing system, where: the pieces of dry ice are retained in the dry ice retention space(s) into which they are introduced by the retainer (s), and $CO_2$ gas produced by sublimation of the dry ice passes out of the retention space(s) into the sample-holding portion of the chamber; the quantity of said solid dry ice pieces is sufficient to maintain a temperature below −50° C. for at least 1 hour when measured 1 inch above the chamber floor in the sample-holding portion; and the sample-holding portion of cryogenic processing system is substantially free of the solid dry ice pieces.

In one aspect the invention provides a gas-permeable dry ice retainer for use in an insulated open-top rectangular parallelepiped chamber of a cryogenic processing system, comprising one or more substantially rectangular and planer barrier elements through which $CO_2$ gas passes and through which solid dry ice pieces do not pass, wherein said planer element is adapted for placement within said chamber such that it is separated from and faces an interior wall of the chamber, forming a retention space between the interior wall and the barrier element into which dry ice may be introduced. In an embodiment the retainer comprises vertical and/or horizontal flanges that position the retainer element such that the flange(s) separate(s) the barrier element from the facing interior wall by a distance equal to the dimension of the flange. In an embodiment the retainer comprises 2 to 4 substantially rectangular and planer barrier elements through which $CO_2$ gas passes and through which solid dry ice pieces do not pass, each barrier element joined orthogonally to the adjacent element(s), and said retainer adapted for placement within said chamber such that each barrier is separated from and faces an interior wall of the chamber, forming a space between the interior wall and the barrier element into which dry ice may be introduced.

In one aspect the invention provides a laser mounting system, comprising: a laser carriage comprising a laser diode electrically connected to a first electrical terminal, and further comprising a first magnet; a mounting plate comprising a second electrical terminal and a second magnet, the second electrical terminal and second magnet being positioned to align with the first electrical terminal and the first magnet when laser carriage is coupled to the mounting plate; a harness adapter having a first surface for receiving an outer surface of a sensor harness and an opposing surface for receiving the mounting plate, the harness adapter being interposed between the harness and the mounting plate; and a lead wire coupled to the second electrical terminal. In some embodiments the laser carriage comprises a pair of laser diodes.

In an embodiment, a front surface of the laser carriage comprises a plane, and wherein a side corner edge of the front surface is angled inwardly in the range of 10°-50°, optionally at approximately 30°, relative to the plane of the front surface, wherein a central axis of the laser diode is angled at approximately 30° relative to the plane of the front surface.

In an embodiment, the laser carriage comprises a first laser diode positioned on a first angled corner of the front surface, and a second laser diode positioned on a second angled corner of the front surface, wherein the first angled corner is opposite the second angled corner on the front surface. In an embodiment, an angle between a central axis of the first laser diode and a central axis of the second laser diode is in the range of 20°-100°, optionally at approximately is approximately 60°.

In an embodiment, laser carriage is selectively removable from the mounting plate. In an embodiment, the harness adapter is permanently attached to the harness. In an embodiment, the mounting plate is removably coupled to the harness adapter via a fastener. In an embodiment, the laser mounting system comprises a magnetic interface between the mounting plate and the laser carriage. In an embodiment the laser mounting system includes a keyed connection between the mounting plate and the laser carriage.

BRIEF DESCRIPTION OF THE DRAWINGS

In order that the manner in which the above-recited and other features and advantages of the invention will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1 shows an exemplary system 100 of an embodiment of the invention and is provided to introduce certain terms used to describe the invention: container 110; container sides 200ab, container bottom 300, walls (interior surfaces) 400ab, floor (interior surface) 500, chamber 600, retainer elements 700ab, dry ice retention spaces 800ab, low temperature zone 900; retainer peripheral structure (back) 1000; and retainer peripheral structure (bottom) 1100, and container deck 1200. Line aa-dd shows the width of the chamber; line bb-cc shows the width of the working area (or "sample-holding portion") of the chamber; line cc-dd delineates dry ice retention space 800b; line aa'-bb delineates dry ice retention space 800a.

FIG. 2C illustrates a perspective showing the retainer element positioned in the chamber of the device, in an embodiment with a collar;

FIG. 2D illustrates a section view of the device shown in FIG. 2C;

Figure 2A:
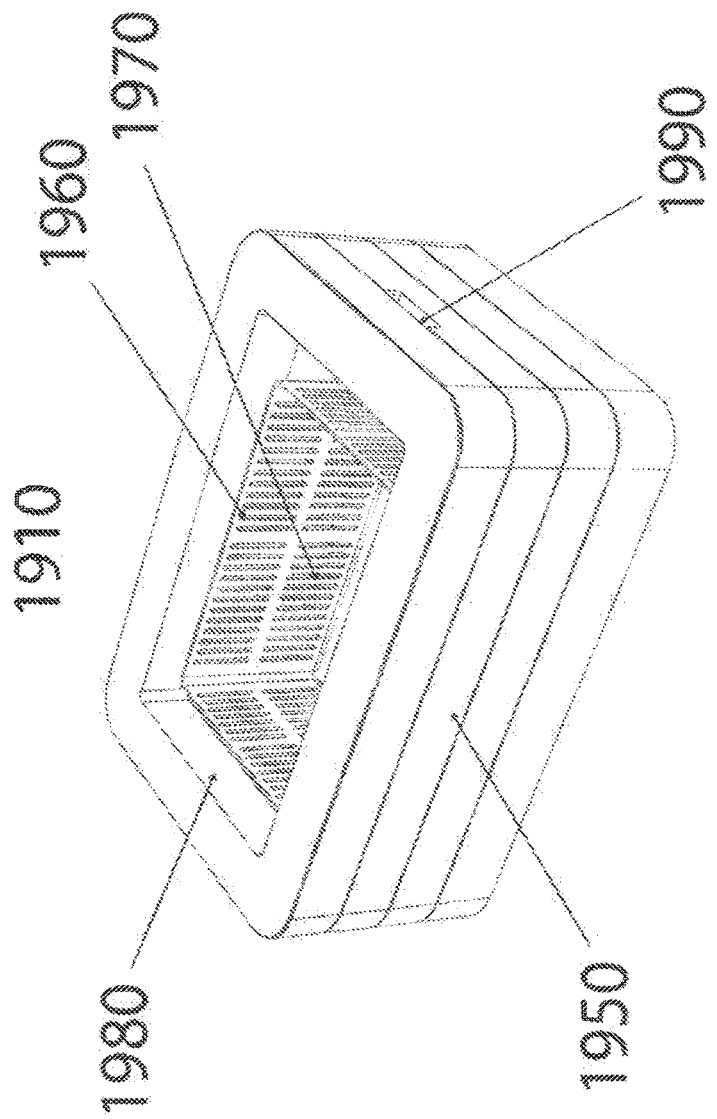
FIG. 2A illustrates a perspective showing the retainer element positioned in the chamber of the device.

Materials stored in a frozen state at low temperature (e.g., −70° C. to −50° C.) often require additional operations such as sorting, inventory, transfer, filling, boxing, labeling, cataloging, shipping, and location confirmation. Such operations typically require time intervals, spatial volumes, and access orientations that prohibit the performance of these operations inside conventional ultra-low temperature storage devices.

In one aspect, the present invention provides cryogenic workstations, or devices, for maintaining samples at an ultra-low temperature. In one aspect the device is used to maintain a low temperature zone that allows a human operator or robotic mechanism located in a zone of higher temperature to conduct extensive operations and manipulations on materials while maintaining them at low temperatures for optimal preservation of sample integrity. In one aspect, a low temperature zone is maintained during loading of a sample into the device. In one aspect the device includes an openable, optionally removable, cover. In one aspect, an ultra-low temperature environment is maintained in the device during transport, shipping or storage of samples.

Cryogenic devices of the invention include a container including a chamber, sometimes called a "cavity," and one or more dry ice retainers disposed within the chamber. The retainer(s) comprise a gas permeable retainer element, and divides the chamber into (i) a sample-holding portion, and (ii) at least one dry ice retention space. When the dry ice retention space is filled with dry ice, the dry ice is confined in the space, in part by the gas permeable retainer element. See, e.g., FIG. 1. Thus confined, the dry ice remains physically separated from materials (e.g., samples) placed in the working area of the chamber. As $CO_2$ gas is formed by sublimation of the dry ice held in the retention space, the gas passes through the gas permeable retainer element into the sample-holding portion of the chamber, producing a low temperature zone in which samples may be processed. As used herein the terms "sample-holding portion" and "working area" of the chamber are used interchangeably.

Guided by this specification, one of ordinary skill in the art can construct a device that, when charged with dry ice, results in a chamber temperature below −50° C. for at least four hours as measured 1-5 inches above the chamber floor in the sample-holding portion of the chamber. Using the device, an operator can have complete and continuous access to the samples during processing, while maintaining the samples at ultra-low temperature.

II. Definitions

The following definitions are provided to better understand the invention.

As used herein "cryogenic processing" refers to processing steps performed on a frozen sample under conditions in which the sample is maintained at a temperature equal to or less than −50° C. In various embodiments, the processing steps may include, without limitation, one or more of the following: receiving, sorting, storage, transport, packaging, labeling, manipulation, filling, boxing, scanning (e.g., for location confirmation), detecting (e.g., for inventory or cataloging), and product testing (e.g., for weld-integrity at low temperature).

As used herein, the terms "sample," "product," "specimen," "object," are used interchangeably and refer to objects or materials maintained at low temperature using the devices and methods according to the invention. "Samples" can include containers (e.g., vials, bottles, tubes, packages, racks, boxes or trays containing vials), materials (e.g., cells, proteins, vaccines, solutions, suspensions) and objects. In some embodiment the samples are containers containing a material of interest (e.g., a vial of frozen cells or a tray comprising a plurality of vials of frozen cells). Exemplary samples for cryogenic processing according to the invention may be described based on their shapes and/or dimensions of which exemplary embodiments include: (i) a cube with dimensions of about 0.1, about 0.5, about 1, about 2, about 3, about 4, about 5, about 6, about 7, about 8, about 9, about 10, about 11, about 12, or more than 12 inches on a side; (ii) a cylinder with a height "a" and a diameter "b," or a rectangle with a height "a", width "b", and depth "c" wherein each of a, b and c has a value independently selected from 0.1, 0.5. 1, 2, 3, 4, 5, 6, 7, 8, 9, 10, 15, 20, 30, and 36 inches.

As used herein, in accord with common usage, reference to a physical dimension of a cryogenic workstation or elements of a workstation, refers to the orientation of the system when in use (e.g., during loading). For example, the "bottom" of an element is the part closest to the ground during normal use; "depth" refers the dimension extending from top to bottom, "length" and "width" refers to the spatial dimensions in a plane parallel to the ground, with "length" being the larger or largest measurement.

As used herein, "chamber path length," refers to the chamber length through which an object can be transported (i.e., from one end to the other, or, in the case of a closed loop, from a starting position back to the same position).

As used herein a retainer is "vertically disposed," in a chamber when the depth of the dry ice retention space completely or partially defined by the retainer is greater than at least one other dimension (e.g., width or diameter) of the retention space.

As used herein "dry ice" refers to carbon dioxide ("$CO_2$") in its frozen (solid) form and may be rendered "$sCO_2$". At normal atmospheric pressures dry ice sublimates at −78.5° C. to produce carbon dioxide gas ("$gCO_2$").

As used herein, "equilibration" is the process of refers to process of lowering the temperature in the low temperature zone from ambient temperature (e.g., 25° C.) to a target temperature (e.g., less than −50° C.). Equilibration generally involves at least partially filling one or more dry ice retention spaces with dry ice. Optionally, the dry ice may be replaced or replenished as it sublimates. In some embodiments, equilibration is carried out with a chamber cover in place.

As used herein "equilibration period" is the time required to reduce the temperature in the low temperature zone from ambient temperature (e.g., 25° C.) to a target temperature (e.g., less than −50° C., less than −60° C., etc.) by introducing dry ice into the dry ice retention space(s).

As used herein, the terms "low temperature zone," "zone of low temperature," "cooling zone," or "cryogenic zone," are used interchangeably to refer to the region of a chamber in which the samples to be maintained in a cold state are held during cryogenic processing.

III. General Features of the Workstation, Container, Chamber, and Retainer

A. Container Properties

FIG. 1 is a schematic of an exemplary system of the invention, and is provided to illustrate certain terms and components described herein. It will be appreciated that the figures herein are illustrative examples and are not intended to limit the invention.

As noted above, the cryogenic device of the invention comprises a container adapted to receive samples (e.g., frozen samples) for cryogenic processing. The container comprises a gas-tight chamber and at least one gas-permeable dry ice retainer element disposed within the chamber. The chamber comprises a chamber floor and one or more chamber wall(s). As used in this context, the terms "floor" and "wall" refer to the interior surfaces of the bottom and side elements, respectively, of the container. As discussed below, the workstation may include a variety of other components and accessories including, without limitation, a cover, temperature sensors, lasers, alarms, sensor harness, laser harness, laser carriage, videographic recorder, and chest freezer tower rack adaptors.

FIG. 2 shows illustrative embodiments of the workstation. FIG. 2A shows a perspective view of device 1910. The container bottom is joined to the container sides 1950 to form a gas-tight chamber 1970 into which the samples are placed. Retainer element 1960 is shown positioned in the chamber. The retainer element is shown with three planar parts with double rows of slots, with each part facing a chamber wall, forming dry ice retention space 1980 between the retainer element and the three chamber walls. The container, cover and deck may be constructed from an insulating material, such as an insulating foam material. Optional handle element 1990 may be used to assist lifting and carrying. Alternatively, the system can be fitted with strap handle, integral protruding handle, wheels, and the like.

Figure 2B:
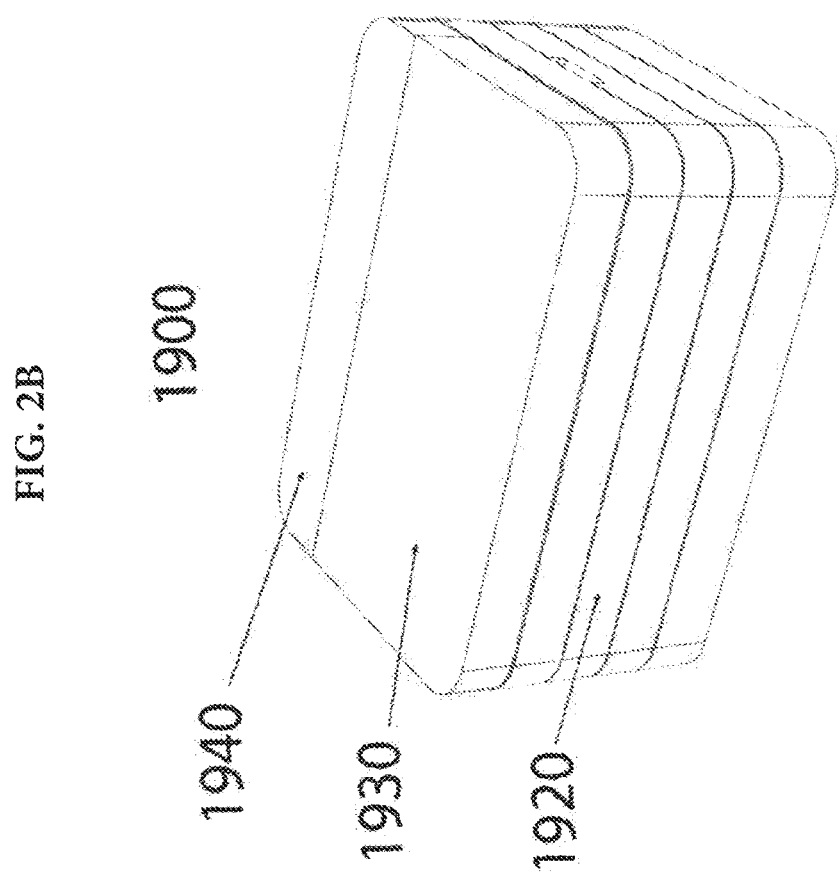
FIG. 2B illustrates an external view of the device shown in FIG. 2A, showing an optional cover.

FIG. 2B shows the exterior of an embodiment of a device 1900. In this illustration, container 1920 is constructed from laminations of an insulating material, such as an insulating foam material. The container 1920 is shown covered by a forward lid element 1930 and a rear element (back deck) 1940. The forward and rear lids may be removed for accessing the chamber as shown in the open chamber configuration illustration 1910. Alternatively, the rear element 1940 may be fixed and cover 1930 may be hinged thereto.

Figure 3D:
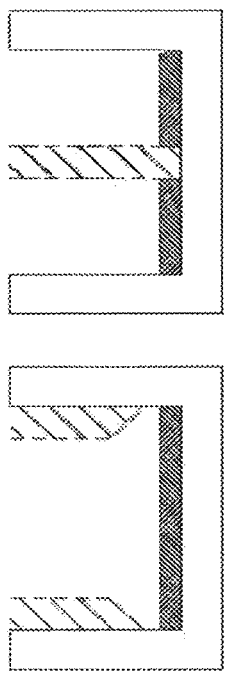
FIG. 3A through FIG. 3P provide schematic cross-sections showing the relative orientations of (i) the chamber floor and wall(s), (ii) dry ice retainer elements, (iii) dry ice retention spaces containing dry ice pieces (cross-hatched), and (iv) the footprint of a low temperature zone (heavy black line).
Figure 3H:
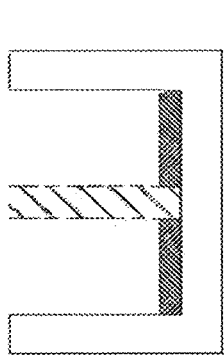
Figure 3C:
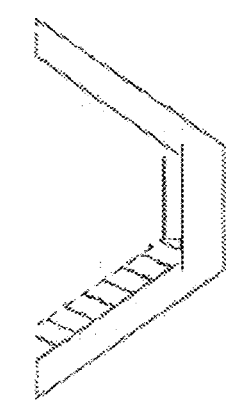
Figure 3G:
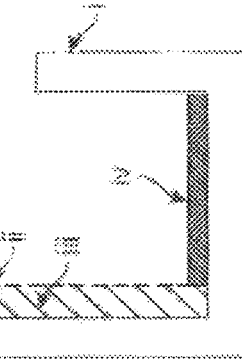
Figure 3K:
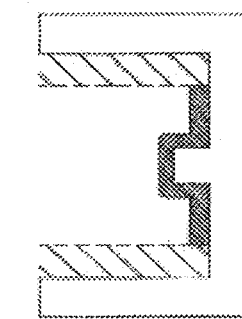
Figure 3B:
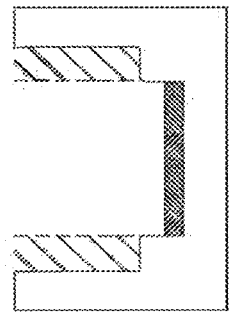
Figure 3F:
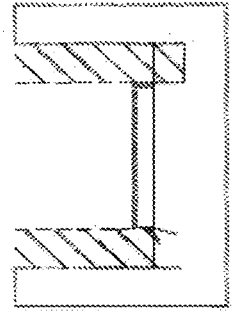
Figure 3J:
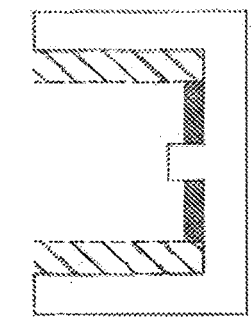
Figure 3A:
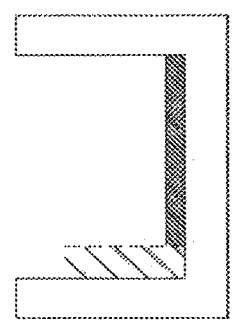
Figure 3E:
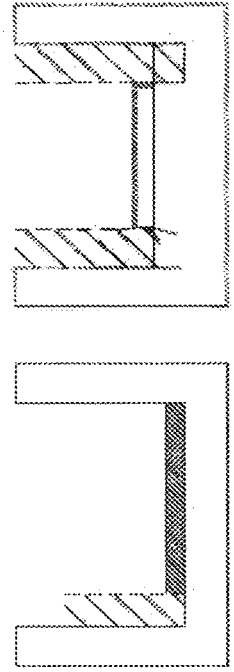
Figure 3I:
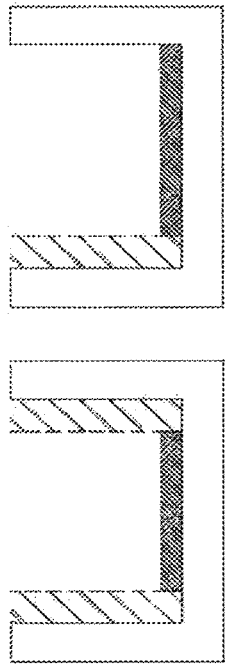
Figure 3L:
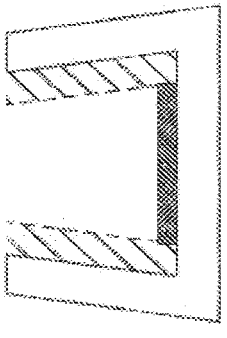
Figure 3M:
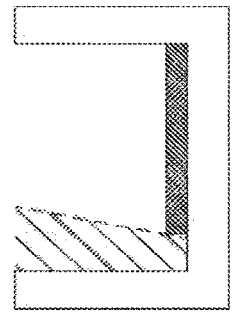
Figure 3N:
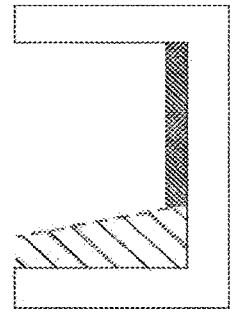
Figure 3O:
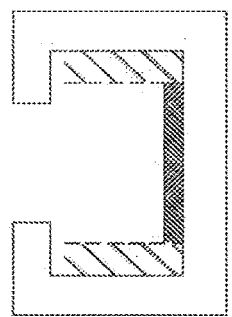
Figure 3P:
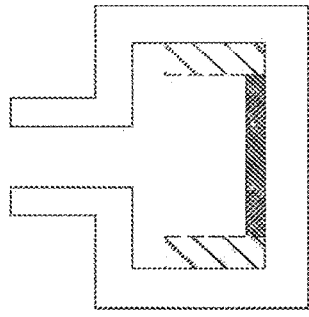

FIG. 2C shows an embodiment in which the chamber opening includes a collar. The figure shows collar 2, collar standoff 8, base assembly 3, and dry ice retainer 4. The collar feature (also shown in FIG. 3O), serves several purposes: (1) The collar fits on, is attached, or is integrated with, for example, the top of the container and reduces the area of the chamber opening such that the direct chamber-to-environment interface area is reduced without significantly restricting the working-area access. In some embodiments, the collar covers at least part (and sometimes all) of the top of the dry ice refrigerant from the inner chamber wall to the retainer while maintaining a gap between the undersurface of the collar and the top of the dry ice retainer. The gap allows for gas circulation from the upper chamber to the dry ice retention area. In some embodiments, the gap may be in the range of about 0.25 inches to about 2 inches. In addition, as the sublimation of the dry ice refrigerant produces carbon dioxide gas, the reduced area of the chamber opening resulting from the collar will increase the velocity of the discharged gas, thereby increasing the back-flushing of atmospheric moisture condensate that forms at the chamber opening. The thickness (or depth) of the collar may vary but is typically in the range of about 1 inch to about 10 inches, often about 2 inches to about 5 inches. As used herein, the inner passage through the collar forming the inner perimeter can be referred to as the "throat" of the collar and generally has a depth equal to the depth of the collar. (2) The collar may also be fitted with an extension (e.g., a rectangular extension) that forms a chimney-like passageway that extends the effective depth of the chamber above a horizontal plane at the top of the dry ice refrigerant, thereby increasing the depth of the zone of temperature transition from the environmental temperature to the upper chamber temperature. See FIG. 3P. The extension or chimney may be, e.g., fit on, be attached to, or integrated with, for example, the collar. The inner portion of the chimney forming the inner perimeter can be referred to as the "throat" of the chimney. As the environmental temperature will typically be in the range of approximately 15 to 35 degrees Celsius, and the upper chamber temperature (i.e., the temperature at the top opening of the chamber at the chamber collar interface) may be in the range of approximately −30 to −60 degrees Celsius, a zero degrees Celsius temperature will be located in the throat of the collar. As atmospheric moisture will precipitate at approximately 0 degrees Celsius, the microcrystal moisture condensate will form in the throat of the collar, and the condensate may either precipitate onto the inner surface of the throat in a short band, or remain suspended in the gas. Suspended microcrystalline moisture may be back-flushed to the environment by the upwelling carbon dioxide gas in the collar throat due to the continuous phase change of the solid refrigerant. Trapping or expulsion of the moisture condensate significantly reduces the accumulation of the crystalized moisture with the chamber and serves to both maintain a clean working area within the chamber and reduce occlusion of the dry ice refrigerant, thereby preserving optimal gas flow. (3) The collar isolates the dry ice in the system from the exterior thereby providing additional protection for the operator and increasing the top surface area of the invention which may be convenient for placement of necessary tools and equipment with which to conduct internal operations. The standoffs (8) rest in direct contact with the dry ice retainer adding support and rigidity to the collar. As used in this context, a stand-off is a load-bearing support feature that protrudes from the underside of the collar and spans the gap between the top of the dry ice retainer and the underside of the collar. The stand-off functions to support a thin foam collar which may distort under load or even under its own weight. In some embodiments, the thickness of the collar provides sufficient rigidity so that the standoff features are not necessary. In some embodiments, the collar is removable. In other embodiments the collar comprises a thickness of insulating material with a tubular extension or chimney that will increase the height the throat passageway. See FIG. 3P. In some embodiments, the height and opening area of the upper portion of the collar can be modified to provide additional system efficiency. In some embodiments, interlocking or stackable collar extensions, adapters, throat constricting or expanding features may be selectively added or removed from the collar or chimney. In some embodiments, mechanical gates or covers may be interfaced with the collar or chimney to allow intermittent access to the chamber, for example to allow infrequent access of a robotic arm into the chamber area.

In some embodiments, fastening features are attached or embedded into the surface of the lid or collar for the purpose of attachment or fixation of bodies to the collar or lid, while in other embodiments the lid or collar comprises recesses 6 and channels 7 that may receive additional equipment such as, and without limitation, tools, temperature and/or humidity monitoring devices, sensors, sensor leads, data loggers, bar code scanners, RFID readers, power supplies, human interface devices, proximity sensors, wireless data link equipment, lighting equipment, image and video equipment, global positioning electronics, and notification and/or alarm equipment. In some embodiments, the recesses and/or channels are integrated into the upper surface of the collar or lid, while in other embodiments, the recesses and/or channels are embedded partially or completely inside the collar or lid. In some embodiments, the passages and/or recesses extend entirely through the thickness of the collar or lid thereby allowing the support, exposure, or protrusion of equipment into the chamber area below. Also shown in FIG. 2C are handle feature 5, and a hole feature for magnet 9. Magnets may be used to attach the collar to the container sides, and/or attach the cover to the collar.

FIG. 2D shows a section view of the device illustrated in FIG. 2C, showing case 11, retainer 4; dry ice retention space 13; collar 2; cover 10, and handle feature 12.

Figure 2E:
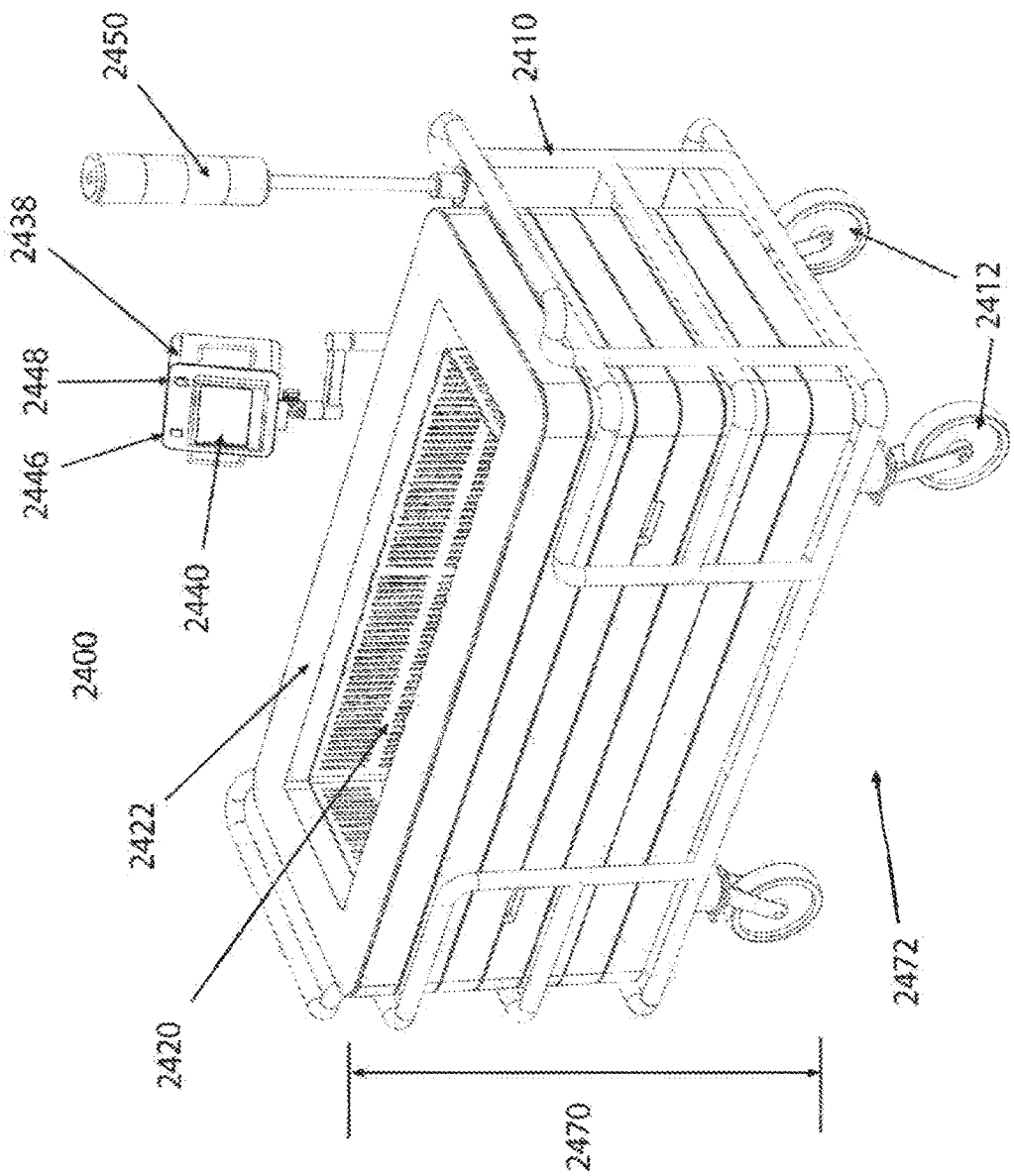
FIG. 2E illustrates a mobile shuttle system including a cryogenic system, according to an embodiment.

FIG. 2E shows a mobile transfer system 2400 used for transferring product vials to final packaging. The mobile transfer system includes a cart 2410 for transporting the device.

Figure 2F:
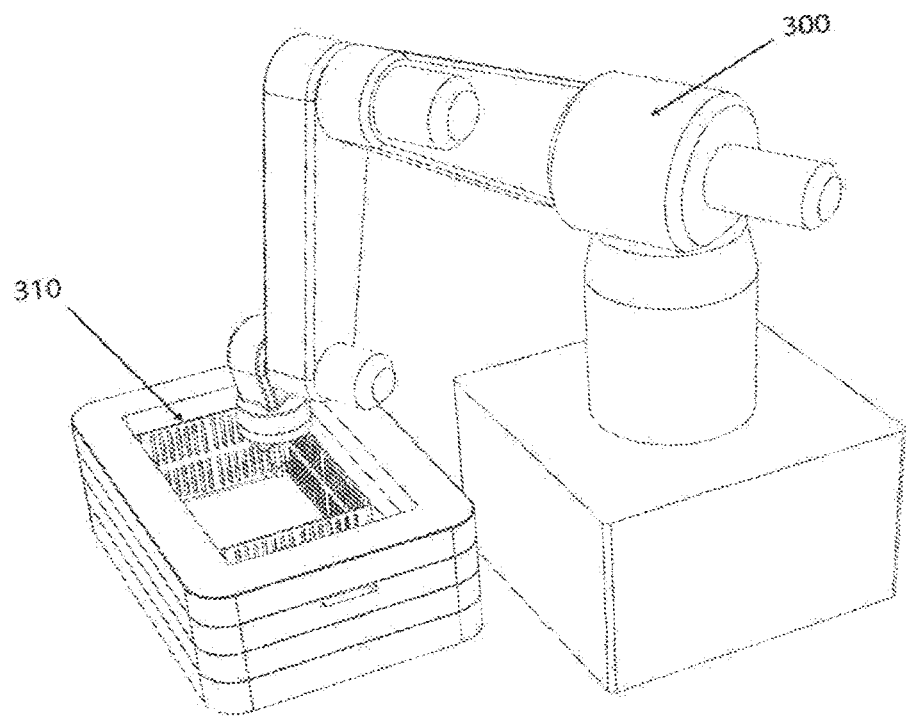
FIG. 2F illustrates a system including a robotic arm configured to manipulate samples in a workstation, according to an embodiment.

FIG. 2F shows a system in which robotic arm 300 is positioned to manipulate samples in the chamber of workstation. Dry ice retainer 310 is positioned within the chamber. In a related embodiment the robotic arm is placed a deck of the workstation.

Figure 2G:
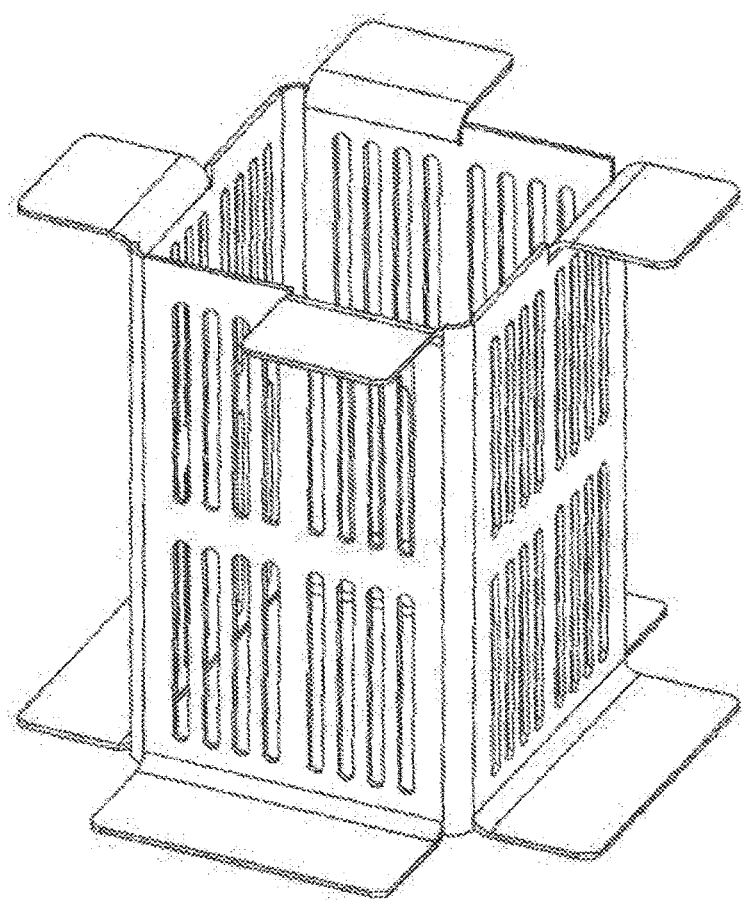
FIG. 2G illustrates a dry ice retainer, according to an embodiment.

FIG. 2G shows an isolated dry ice retainer suitable for use with a container sized to match the footprint of the bottom flanges.

The container of a cryogenic device of the invention may have any desired exterior dimensions that are compatible with the teachings of the present invention and the intended use of the device. In some instances, the container comprises an outer length from approximately 24 inches to 120 inches, or greater, such as approximately 36 inches to approximately 96 inches, and in one embodiment an outer length of 66 inches. In another embodiment, the container comprises an outer length of 35 inches. The container further comprises an outer width from approximately 12 inches to approximately 40 inches, such as from approximately 18 inches to approximately 32 inches, and in one embodiment an outer width of 28 inches. In another embodiment, the container comprises an outer width of 24 inches. In some instances, the container comprises an exterior height from approximately 6 inches to approximately 32 inches, such as from approximately 12 inches to approximately 28 inches, and in one embodiment an exterior height of 15 inches. In another embodiment, the container comprises an exterior height of 26.5 inches. For example, in one embodiment, the overall dimensions of the embodiment shown are 35 inches in length by 24 inches in width and 15.5 inches in height at the top surface of the cover. The interior chamber dimensions measure 27 inches in length by 16 inches in width by 9.5 inches in depth.

The container may be constructed in any manner and from any material or combination of materials consistent with its intended functions. For example, the chamber may be formed from a single monolithic material by punching, molding or milling to form a cavity; may be formed by assembling side and bottom pieces together (e.g., joining four side elements and a bottom element), may be assembled from modular subunits, or various combinations of these approaches. In another embodiment, the container may be constructed from an inner and outer shell with the volume between the shells occupied by molded insulating foam.

In some instances, the container comprises a lamination of two or more sections. In one embodiment, the container comprises a lamination of three middle sections coupled to a base and configured to receive a lid (see FIG. 2B). The middle sections may each comprise an individual thickness that provides a desired chamber depth following lamination. For example, in some instances each middle section comprises an individual thickness from approximately 2 inches to approximately 6 inches, from approximately 2.5 inches to 4 inches, and in one embodiment an individual thickness of 3.25 inches. In another embodiment, each middle section has an individual thickness of 3 inches.

The chamber is insulated to maintain the low temperature. The sides and bottom of the container can be constructed from an insulating material. Exemplary insulating materials include cross-linked polyethylene foam, urethane foam, a plastic-covered urethane foam, a styrene foam, a plastic-covered styrene foam, a polyvinyl foam, or a blended polymer foam (including blends of any of the preceding materials as well as plastic-skinned blends). Many other suitable materials are known in the art. In some embodiments the insulating material has a thermal conductivity below 0.2 watts per meter kelvin. In some embodiments the insulating material is selected so that when the temperature of the chamber floor is in the range −70° C. to −50° C. the temperature of the exterior surface of the container is greater than 15° C.

The wall thickness of the container may be selected to optimize the insulative properties of the device. In some instances, the container comprises a wall thickness from approximately 2 inches to approximately 12 inches, from approximately 8 inches to approximately 10 inches, and in one embodiment a wall thickness of 6 inches. Likewise, the bottom or base of the container may have a thickness selected to optimize the insulative properties of the device. For example, in some instances the container bottom comprises a thickness from approximately 2 inches to approximately 8 inches, from approximately 2.5 inches to 4 inches, and in one embodiment a thickness of 3.5 inches. In embodiments in which a cover, or lid, is present, the cover may have a thickness selected to optimize the insulative properties of the device, and otherwise be constructed to have insulating properties (e.g., comprising insulating material with thermal conductivity below 0.2 watts per meter kelvin). In some instances, the cover comprises a thickness from approximately 1 inch to approximately 2 inches, and in one embodiment a thickness of 2.5 inches.

In some embodiments, all or at least the lower portion of the chamber is "gas-tight." That is, carbon dioxide gas formed by sublimation of dry ice in the chamber does not readily pass through the chamber walls or floor out of the chamber. As used in this context, "does not readily pass through" means that less than when the chamber is filled with $CO_2$ gas, less than 5% per hours, preferably less than 1% per hour, passes through the chamber walls or floor of the "gas-tight" region. Carbon dioxide gas can circulate upward and out of the chamber through the open top portion (e.g., when the chamber is uncovered).

B. Chamber Properties

The interior shape of the chamber may vary depending on the needs of the operator. For illustration, the shape of the chamber (i.e., the cavity) may be a regular or irregular polyhedron such as a cuboid, triangular, rectangular, hexagonal, pentagonal, trapezoidal, trapezium, rhomboid or other polyhedral prism, including right and oblique prisms. The chamber may have curved surfaces. The shape of the chamber may be an ovoid cylinder such as a right circular cylinder. The chamber may have a cross-section that is a regular or irregular quadrilaterals or which varies along the length of the chamber. Common chamber forms include rectangular prism, right circular cylinder, trapezoidal prism, isosceles trapezoidal prism. For illustration and not limitation, other exemplary shapes can be inferred from the cross-sections shown in FIG. 3. In some embodiments the chamber comprises four interior walls.

In some embodiments, the size of the top opening (e.g., with the cover absent) is substantial, to permit ready access to the chamber and particularly the low temperature zone. In some embodiments, the opening has about the same size as the chamber floor, as illustrated in FIG. 1 and FIG. 2A. In some applications, general the area of the opening is about 80% to about 120% of the area of the floor. See, e.g., FIG. 3G and FIG. 3N. In other embodiments the opening is about 90% to about 110%, or about 95% to about 105% of the area of the floor. In other embodiments, the opening is partially restricted to allow the necessary access while minimizing the area of direct interface of the chamber gas with the external atmospheric gas. See, e.g., FIG. 3O and FIG. 3P. In some embodiments the opening is about 50% to about 90% of the area of the floor.

In some embodiments the walls and floor of the chamber are substantially planar (flat) in cross section. It will be appreciated that a flat wall or floor may be textured or patterned. Further, a floor may include an array of indentations such as pockets or tracks, or the like, to receive, hold and/or transport samples. As illustrated in FIG. 3 the floor may include a raised or depressed region which may be within (FIG. 3J) or outside of (FIG. 3I) the low temperature zone. In some embodiments, the chamber floor is adapted to transport samples and, for example, may comprise conveyor mechanisms such as bearings or belt or tray conveyors. In some embodiments the chamber is configured to hold tray stacks or storage boxes.

The present invention is highly scalable and the dimensions of the chamber can vary broadly according to the needs of the operator. For example, it is possible to construct a chamber of substantial length in accordance with the invention. In one embodiment the device is suitable for simultaneous use by two individuals working side by side, as useful for a two-step process. See, e.g., FIG. 7.

For example, the chamber may have at least one dimension (width, length, depth, or diameter) in the range of 2 inches, or smaller, to 10 feet (or longer). In one embodiment, the device has a chamber volume of 0.1 cubic feet to 2 cubic feet, such as 0.2 cubic feet to 1 cubic foot, sometimes 0.25 cubic feet to 0.5 cubic feet. In one embodiment, the device has a chamber volume of 0.1 cubic feet to 27 cubic feet, such as 1 cubic foot to 16 cubic feet, and sometimes 1 cubic foot to 8 cubic feet. In other embodiments, the device has a chamber volume of 4 cubic feet to 200 cubic feet, such as 8 cubic feet to 100 cubic feet.

For example and without limitation, for use by human operators workstations may have a chamber depth of about 5 inches to about 36 inches, more often about 10 inches to about 24 inches. In some instances, the chamber comprises a length of from approximately 20 inches to 116 inches, or greater, from approximately 32 inches to approximately 92 inches, and in one embodiment an inner length of 54 inches. In another embodiment, the chamber comprises a length of 27 inches. The chamber further comprises a width from approximately 8 inches to approximately 36 inches, from approximately 14 inches to approximately 28 inches, and in one embodiment an inner width 16 inches. In some instances, the chamber further comprises a depth from approximately 6 inches to approximately 24 inches, from approximately 8 inches to approximately 22.5 inches, and in one embodiment a depth of 10 inches. In another embodiment, the chamber comprises a depth of 9.5 inches. In yet another embodiment, the chamber comprises a depth of 21.5 inches. In yet another embodiment, the chamber comprises a depth of greater than 30 inches, e.g., 50 inches. In exemplary embodiments the chamber dimensions are (l-w-d) 54×16×9.5 (with working area dimensions of 48×13.25× 9.5); 54×16×13.5 (with working area dimensions of 48×13.25×13.5); or 27×16×9.5 (with working area dimensions of 21×13.25×9.5). Exemplary chamber volumes include, without limitation (in cubic inches) 3000-5000, 4000-6000, 5000-7000, 6500-8500, 7,000-9,000, 8,000-11,000, 10,000-12,000. In some embodiments the chamber volume is larger than 5,000, larger than 10,000, larger than 20,000, or larger than 40,000 cubic inches.

Samples may be manipulated in the low temperature zone by, for example, human operators, by robots, or both together. In certain embodiments the dimensions are adapted for operation by humans. In such applications it is preferable that the width and depth of the chamber allow the operator to reach into the cavity (with or without use of tools to extend reach) and manipulate the chamber contents.

In some embodiments the device is scaled to be easily carried by one person. For such applications, the outside dimensions of the device are generally not more than about 30×30×30 inches, such as about 22 inches deep×about 36 inches wide×about 22 inches high. A typical payload area for a hand-carried device could be, for example, accommodate up to 8 cryoboxes (each 2×5×5 inches). For example, such an embodiment could have internal chamber dimensions of 6.5 inches deep×11.6 inches wide×9 inches high. A smaller version might be scaled to carry a sample with 2×2×2 inches (e.g., a single vial) with outside dimensions of, for example, about 6" deep×about 8" wide×about 5" high.

Figure 4A:
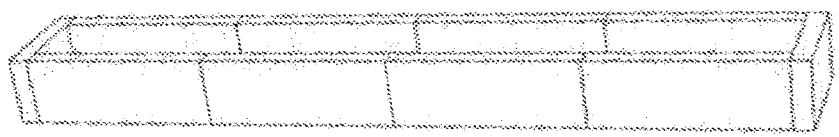
FIG. 4A illustrates a linear trough configuration.
Figure 4B:
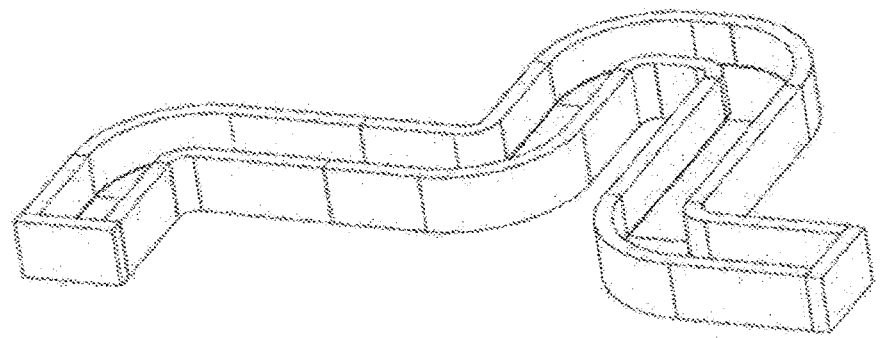
FIG. 4B illustrates a serpentine trough configuration.
Figure 4C:
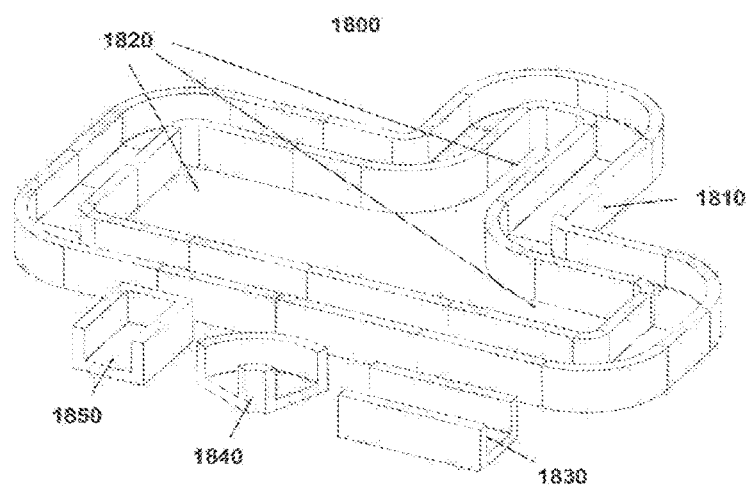
FIG. 4C illustrates a closed loop configuration, illustrating that a container housing may be produced in modular format and assembled.

As noted above, the chamber has an open (or openable) top portion for user access to the interior of the chamber, e.g., for loading or other manipulation of sample. Thus, the chamber may be described as box or trough having an extended open-top cavity in which cryogenic processing steps take place. In some embodiments the chamber has a "trough configuration," meaning the chamber has a chamber path length that is more than four times as long of the width of the chamber. FIG. 4A through FIG. 4D illustrate trough embodiments. In some embodiments the chamber can be described as a linear trough (FIG. 4A), a serpentine trough (FIG. 4B), or a zigzag trough. In some embodiments the trough may be branched. In some embodiments a branched trough has a single intersection (e.g., a "Y-shaped" or "T-shaped" trough). In some embodiments the trough forms a closed or continuous loop. FIG. 4C shows an illustrative layout 1800 of a trough container raceway 1810. The trough system comprises three U-loops 1820 of various sizes in which personnel or robotic elements may be stationed. The construction of the trough raceway is modular, comprising straight modules 1830 and elbow modules 1840. The trough terminal module 1850 shown would be used as end-pieces in an open loop configuration.

Figure 4D:
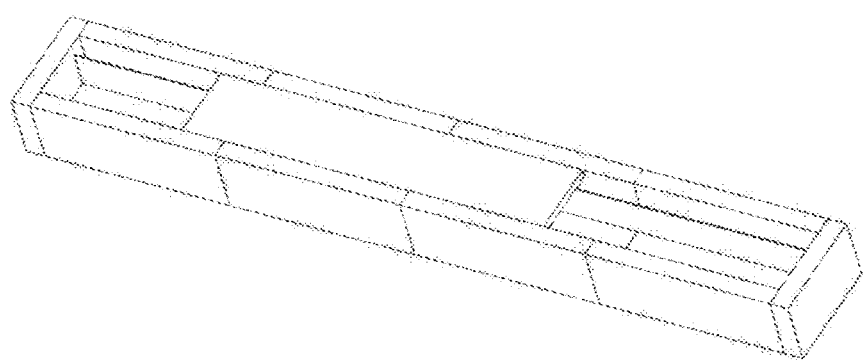
FIG. 4D illustrates a "partially covered" embodiment.

In some embodiments the trough forms an annular loop. In some embodiments, the loop comprises four linear segments, having the path defined by two concentric squares. In some embodiments, some portions of the chamber are covered and other portions are open (FIG. 4D). As used herein, "chamber path length" refers to the distance through which an object can be transported in the chamber (i.e., from one end to the other, or, in the case of a closed loop, from a starting position back to the same position). For illustration, rectangular chamber with an overall length dimension of 4 feet also has a 4 foot chamber path length. In contrast, a serpentine or ring-shaped chamber with a 4 foot overall dimension will have a longer path length. For example, the path length of 4-foot diameter a ring-shaped (annular) chamber is about 12.5 feet (the circumference of the larger of the two concentric circles defined by walls of the chamber).

Bends can be introduced into the long container to accommodate floor layout plans, production flow requirements, and process sequence optimization. A complete loop of trough-shaped containers can be constructed in an unlimited variety of layouts and sizes in accordance with the invention. For example, for robotic arm activity, a circular (ring shaped) trough may be an optimal configuration so as to take advantage of a central robotic pivot point.

In some embodiments the chamber has a trough configuration with a chamber path length that is more than five times, more than six times, or more than 8 times the width of the chamber.

In some embodiments the chamber has a trough configuration with a chamber path length of more than 3 feet, more than 6 feet or more than 10 feet. In some embodiments, the chamber length is 3 to 30 feet, such as 5 to 20 feet, such as 8 to 12 feet.

In some embodiments, multiple containers or container parts may be constructed in with one or more side-walls modified such that two or more containers or parts can be joined to form longer or more complex modular assemblies allowing a continuous well or trough of low temperature gas. See FIG. 4C. As used herein, "modular" has its normal meaning of employing or involving a module or modules as the basis of design or construction. In the context of the invention, the container is constructed from a selection of preformed modules that can be combined in a variety of ways to provide containers with a variety of structure and chamber paths and path lengths. Such arrangements can allow the construction of extended or complex working systems in which operations may be conducted without the need to expose materials contained therein to external environments or temperatures. In some embodiments, the containers may be joined, for example and without limitation, an internal or external flange joint, an adhesive joint, a magnetic joint, a fusion weld, a clamp, or an integral permanent or reversibly attachable interlocking feature. In some embodiments, the multiple section container structures form a linear structure, while in other embodiments the containers form complex pathways, for example and without limitation, to allow enhanced access or strategic placement of personnel, machinery, or robotic systems. In some embodiments, the joined containers form a self-intersecting assembly allowing, for example and without limitation, a robotic arm to circumnavigate the container from a central location without removing portions of the arm from the cold gas interior. In other embodiments, the self-intersecting trough is formed from a single piece of material such as, for example and without limitation, a molded or machined foam trough. In some embodiments, one or more of the joining containers of an extended system may be covered. In other embodiments, one or more joined containers may not comprise a coolant tank, for example and without limitation, to act as adapters, extenders, joints, elbows, or bends in a continuous chamber system.

C. Properties of Retainers and Dry Ice Retention Spaces

As noted in Section 1, above, the dry ice retainer divides the chamber into (i) a sample-holding portion, and (ii) at least one dry ice retention space. The retainer functions to hold or confine dry ice in the "dry ice retention space(s)," while allowing $CO_2$ gas produced by sublimation of the dry ice to move out of the retention space, through the dry ice retainer element, into the sample-holding portion of the chamber. The retainer may hold dry ice against one or more than one inner walls (e.g., at least 2, at least 3 or at least 4 inner walls). The system comprising the retainer and dry ice can produce a "low temperature zone" in the sample holding portion of the chamber. The low temperature zone may extend, for example, 1 to 10 inches or higher, above the floor of the chamber in a system in which the cover is absent or open. Because dry ice is largely or almost entirely confined to the dry ice retention space(s), the sample-holding portion, including the low temperature zone, is free or substantially free from dry ice. Thus, samples positioned in the low temperature zone are maintained in the desired temperature range by contact with $CO_2$ gas, rather than by contact with dry ice.

By manipulating or storing samples within the low temperature zone, it is possible to avoid or reduce exposure to temperate spikes or fluctuations. For example, by loading samples into the low temperature zone of a device, transient temperature fluctuations are avoided. In some embodiments after manipulation (e.g., loading) the device cover is closed, typically resulting in equilibration of temperature within the chamber. When the cover is opened or removed, samples within the low temperature zone remain at the target temperature.

A retainer comprises a gas permeable "retainer element" and optionally, one or more "retainer peripheral structures." Generally, the retainer element comprises one or more rigid walls with holes or openings. The holes (e.g., perforations) allow $CO_2$ gas to pass through the retainer element, but are sized to impede movement of dry ice pieces from the retention space into the working area portion. "Retainer peripheral structures" may be used to position the retainer element in the chamber and/or serve as a barrier retaining dry ice pieces in a dry ice retention space. Side and bottom flanges are examples retainer peripheral structures. Peripheral structures may include openings through which gas flows or may be gas impermeable.

Generally, the retainer, and the dry ice retention space wholly or partially defined by the retainer, is vertically disposed within the chamber. This orientation allows direct access to the chamber floor through the top portion of the container (e.g., access is not blocked by a horizontally oriented retainer). Appropriate positioning allows the human operator or robot to reach through the open top into the cavity to manipulate the samples in the chamber and specifically, samples in the low temperature zone of the chamber. Further, the orientation and position of the retainer contributes to the function of the retainer in producing the sustained ultra-low temperature in the low temperature zone of the chamber by allowing the air or air-$CO_2$ gas mixture in the chamber to fall downward through the sublimating dry ice in the retention space. The cooling effect of the vertically disposed retention space is amplified by a long, tortuous flow path. This design favors heat exchange between the dry ice and the gas flowing over dry ice, and enhances the admixing of the −78° C. $CO_2$ gas coming off of the dry ice with the gas stream, resulting in efficient cooling. In some embodiments the retainer is mounted on the chamber wall.

Typically, the vertically disposed retention space has a depth that is at least 2-fold, more often at least 3-fold, very often at least 4-fold, and sometimes at least 5-fold, at least 6-fold or at least 7-fold the width of the space (e.g., the distance between the retainer element and the chamber wall).

A retainer element may be made from any material consistent with the intended function of the retainer. In some embodiments the material is relatively rigid. Suitable materials include metal (e.g., steel, stainless steel, aluminum, aluminum alloy, copper or copper alloy), cold-tolerant ceramic, plastic, cardboard, or the like. In some embodiments the material is a thermoconductive material, such as anodized aluminum. In some embodiments the retainer element is relatively thin (e.g., as less than 1, less than 0.5, or less than 0.25 inches thick).

The preferred size of the holes or openings in the retainer element (e.g., slots, pores, apertures, perforations, gaps, vents or the like) will depend on a variety of factors, including the dimensions of dry ice pieces used in the operation of the cryogenic processing system. The holes are preferably small enough to retain the dry ice pieces loaded into the dry ice retention spaces. Because sublimation tends to produce dry ice aggregates in some embodiments a portion of the holes may be larger than the dry ice pieces, or larger than the smaller (residual) pieces produced in the sublimation process. In some embodiments the retainer element holes are sized to retain at least some of such residual pieces. In some embodiments, the retainer is designed so that the residual dry ice pieces drop into a compartment or are otherwise prevented from passing through the retainer element into the working area space.

The holes can be any shape consistent with the function of the device. In some embodiments the holes are of uniform size and/or uniform shape and/or are present in a specific pattern, such as a rectilinear pattern. In some embodiments the holes are slots having a length (vertical dimension) of 3 to 6 inches (e.g., 3.5 inches or 4 inches) and a width of 0.3 to 0.5 inches (e.g., 0.313 to 0.375 inches; e.g., 0.313 inches). In some embodiments the holes are slots with a length to width ratio in the range 10:1 to 20:1. In some embodiments the retainer element comprises two or more vertically stacked rows of slots, wherein each slot comprises a width of 0.313 inches and a length of 4.0 inches.

In some embodiments the retainer element is constructed from material (e.g., aluminum) that, but for the holes, is not gas permeable. In some embodiments, the retainer element comprises holes of a size and distribution such that the non-permeable portion of the retainer element comprises the majority of the retainer element area (e.g., at least 51%, sometimes at least 60%, at least 70%, or at least 80%). In some embodiments, the retainer element comprises holes of a size and distribution such that the non-permeable portion of the retainer element comprises less than 50%, less than 40%, less than 30% or less than 20% of the surface area.

Each dry ice retention space is defined by the retainer or by the retainer in combination with chamber walls and/or the chamber floor. A variety of retention space geometries are contemplated. As already noted, a workstation of the invention may comprise multiple retainers and multiple dry ice retention spaces. However, for clarity, the following discussion refers to a single dry ice retention element/retainer and a single dry ice retention space. In some embodiments the total volume of the dry ice retention space(s) is less than the volume of the sample-holding portion. For example, the total volume of the dry ice retention space(s) may be less than about 0.9-fold, less than about 0.8-fold, less than about 0.7-fold, less than about 0.6-fold, less than about 0.5-fold, less than about 0.4-fold, less than about 0.3-fold, less than about 0.2-fold, or less than about 0.1-fold the volume of the sample-holding portion.

Figure 5A:
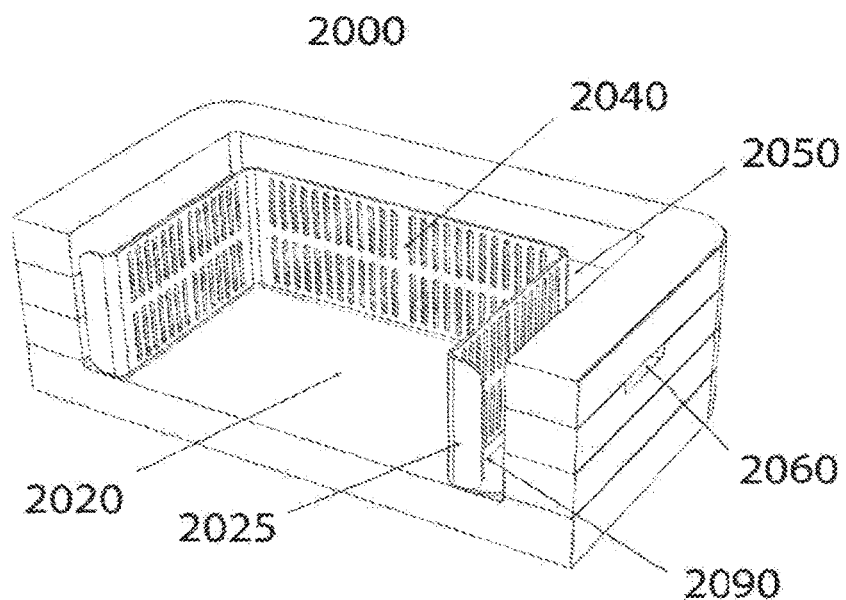
FIG. 5A shows a cross-section of an embodiment in which a retainer element 2070 faces three walls of a four-walled chamber.

In one embodiment the dry ice retainer element is generally planar or flat. In an embodiment, the dry ice retainer element is separated from and faces a chamber wall, and a dry ice retention space, into which dry ice may be introduced, is disposed between the wall and the retainer element. The retainer element may be in close proximity to the wall (e.g., separated by less than 8 inches, less than 5 inches or less than 3 inches). In some embodiments the retainer is separated from the chamber wall by a distance that is less than 30%, less than 20% or less than 10% of the chamber width. FIG. 2A and FIG. 5A illustrate an example of this arrangement. Referring to FIG. 5A, the system 2000 is shown in cross section. The retainer 2040 is positioned in the chamber by interaction of the retainer peripheral structures 2025 (vertical flanges) with the front inner wall of the chamber. The vertical flanges also contribute to retention of the dry ice in the dry ice retention space. In the particular example shown in FIG. 5A, the vertical flanges 2025 do not completely retain the dry ice which, but for the front chamber wall, can spill out through gap 2090. In some embodiments, retainer comprises peripheral structures that form a complete barrier to the passage of dry ice out of the dry ice retention space. In such embodiments, the dry ice retention space is bounded by the peripheral structure.

Figure 5B:
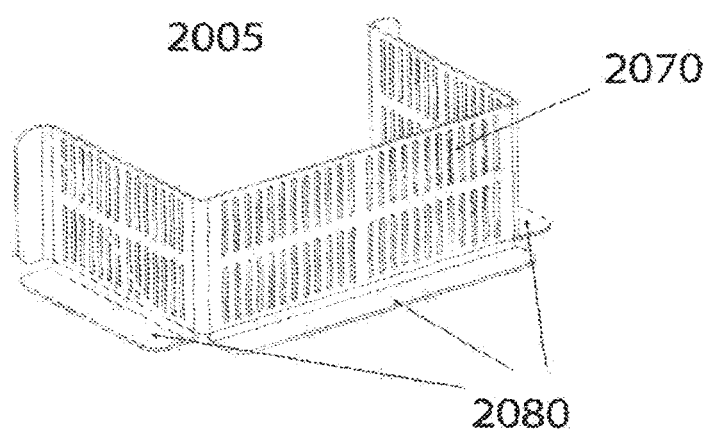
FIG. 5B shows an isolated view of a dry ice retainer element.

In FIG. 5B, the reverse angle perspective of the retainer shows retainer peripheral structures 2080 (horizontal flanges). The retainer 2040 is positioned in the chamber by interaction of the retainer peripheral structures 2025 and 2080 with the chamber walls and floor. The flanges also contribute to retention of the dry ice in the dry ice retention space, and contribute to cooling the chamber. Dry ice pellets and fragments readily form aggregates that prevent a uniform and consistent settling process. As dry ice sublimation reduces the physical volume of the solid $CO_2$, a gap between the dry ice refrigerant and the retainer wall may quickly develop thereby interrupting the thermal conduction pathway between the solid retainer and the solid dry ice. As the weight of the dry ice confined between the retainer and the cavity wall forces the dry ice to be in constant and close contact with the flange elements 2080, an efficient thermal conduction pathway between the vertical retainer walls and the dry ice refrigerant is ensured. The thermally conductive pathway through the retainer to the dry ice refrigerant lowers the temperature of the retainer and allows the retainer to participate in efficient heat exchange with the gas in the cavity thereby assisting in the lowering of the cavity temperature.

The retainer may be fixedly or removably positioned in the chamber. In some embodiments, the chamber is compatible with a plurality of removable retainers, where each retainer has different properties. Properties may include different dimensions (e.g., selected to accommodate a different volume of dry ice and/or dry ice pieces of different sizes or shapes). In FIG. 5A and FIG. 5B, the width of the horizontal flanges 2080 and vertical flanges 2025 determines (in part) the position of the retainer in the chamber, and thereby determines (in part) the position and volume of the dry ice retention space. In some embodiments, the retainer is removably positioned in the interior of the chamber and the container is compatible with a plurality of different retainers with different properties. In some embodiments, the different retainers comprise flanges having different dimensions.

FIG. 5A illustrates a retainer that retains vertically disposed dry ice around three sides of a rectangular parallelepiped. In other embodiments, one or more retainers are adapted to retain vertically disposed dry ice around at least one, at least 2, at least 3, or at least 4, or only one, only two, only three or all four sides of the rectangular parallelepiped, or, analogously, one or more sides of chambers with different geometry. For example, in a serpentine or annular trough, a retainer may extend around the entire circumference, or one or more retainers may extend around a portion or multiple portions of the circumference. See, e.g., FIG. 3. Thus, in contrast to the embodiment of FIG. 5A, which illustrates a single retainer that retains vertically disposed dry ice around multiple walls, in another embodiments multiple different retainers may be used to retain dry ice at various positions within the chamber. For example, two different retainers may be disposed on opposite walls of the chamber.

Further, in some embodiments the retainer is constructed so that the dry ice retention space extends along only a portion of a chamber wall. In one example, the retainer comprises an overall height that is less than an inner height of the chamber. See FIG. 3E. In one embodiment a chamber has a depth of 10.25 inches, and retainer comprises an overall height of 9 inches. Thus, the top of the retainer is 1.25 inches below the top opening of the container. In another embodiment, a chamber has a depth of approximately 22 inches, and retainer comprises an overall height of 21 inches.

Likewise, the retainer may not extend from the top of the chamber to the floor, but may cover only a portion of the depth dimension of the wall. Thus, in some embodiments, the dry ice retention space extends from the floor to a position below the top of the chamber and/or could extend from the top of the chamber wall to a position above the floor. See FIG. 3C. Likewise, the retainer could extend laterally across only a portion of a wall.

As illustrated in FIG. 5A, in some embodiments the dry ice retention spaces may be bounded by the retainer element, an interior wall(s) of the chamber, the chamber floor (or bottom flanges of the retainer) and, if the retainer does not cover the entire perimeter of the chamber and is not bounded at each side by walls, side flanges of the retainer.

In view 2005, the reverse angle perspective of the retainer shows the three horizontal flanges 2080 on the retainer 2070 that position the retainer in the chamber, thereby forming the gap 2050 that will receive the dry ice. The space between the foam (outside wall of the device) and the retainer is filled with dry ice, and in a short while, the interior temperature drops to the desired working range. With devices of this type, a 5 inch depth of gas at a temperature under −50 degrees C. can be achieved. This device, as any of the devices of the invention, can have a lid to reduce heating during periods of non-use. In some embodiment, temperature probes are positioned only at the top of the desired working space (e.g., 5-10 inches from the floor of the device). If the temperatures reported by probes are within compliance, then so is the entire working area. Temperature probe wire leads can be routed through channels 2015 to the front side of the chamber interior to avoid interference with the retainer.

It has been believed that the sublimation temperature of dry ice (−78 degrees) C.) is the lower limit of temperatures that may be achieved with systems of the invention. However, surprisingly, lower chamber temperatures have been measured in devices of the invention. Thus, in some embodiments the devices of the invention, when charged with dry ice and with the cover on, produce a temperature zone colder than −78 degrees C. (such as −79 degrees or lower, −80 degrees or lower, −85 degrees or lower, or −90 degrees or lower). Without intending to be bound to any particular mechanism it is believed that convection (including a slow influx of exterior atmosphere and/or a very slow leak of gas from the chamber) contributes to this observation.

In an alternative embodiment, illustrated in FIG. 1, the dry ice retention space 800a is bounded by a bucket or basket-like retainer including the gas permeable retainer element 700a and peripheral structures 1100 (bottom), 1000 (back), and 1500 (sides; not shown). Retainers of this design can be pre-loaded with dry ice prior to introduction of the retainer into the chamber.

In various embodiments, the system may comprise one retainer (i.e. a single connected unit that may have more than one retainer element) or more than one retainer. In some embodiments, the system comprises more than one retainer, such as 2-10 retainers, 4-10 retainers, 6-10 retainers or more than one retainer.

As noted, in some embodiments, dry ice retention spaces are disposed along only a portion of the chamber length or chamber path length. In some embodiments dry ice retention spaces are disposed along less than 90% of the path length, less than 70%, or less than 50% of the path length, such as from 10-90% of the length, from 20-80% of the length, or from 50-100% of the length. In some embodiments only certain segments, corresponding to less than the entire chamber floor, are maintained at low temperature. FIG. 4D illustrates a closed loop channel in which only a portion of the channel path comprises dry ice retention spaces, with other processes being carried out in other parts of the channel.

Figure 18:
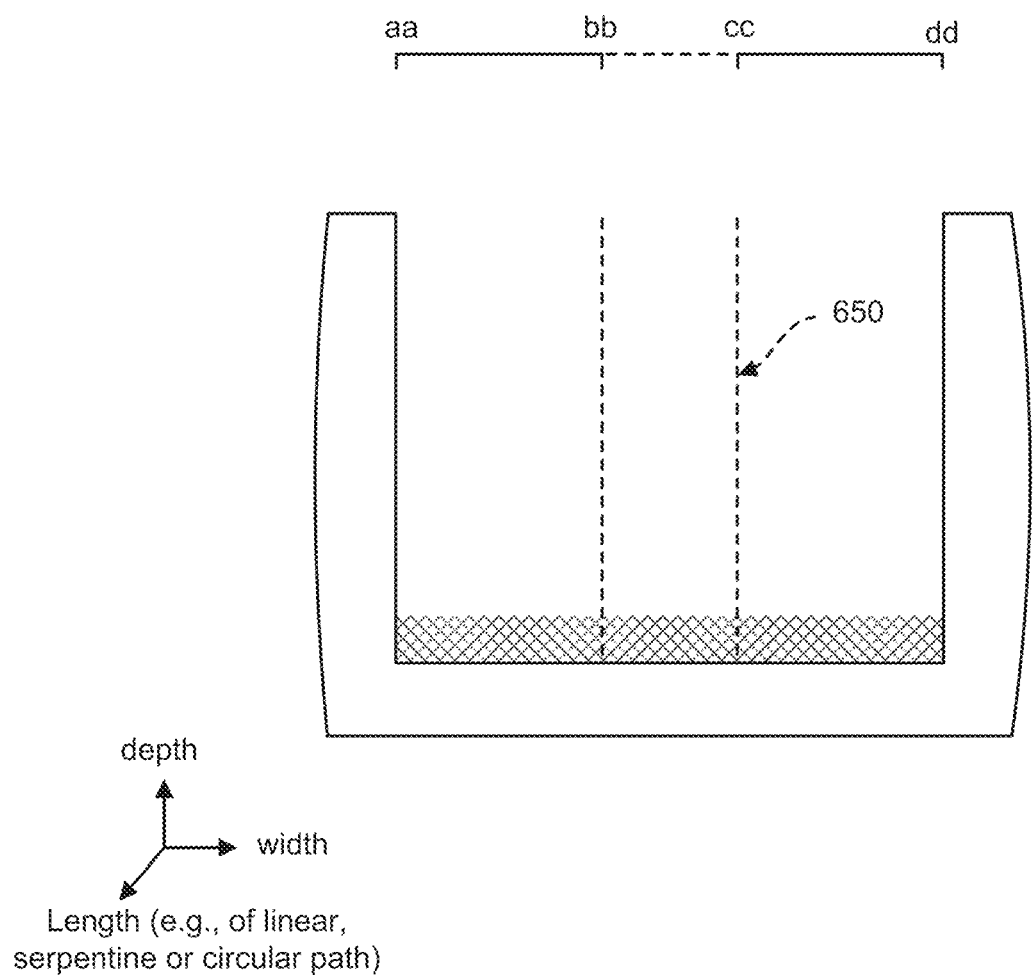
FIG. 18 shows an embodiment of the invention with a dry ice retention space fashioned as a free standing column.
Figure 19:
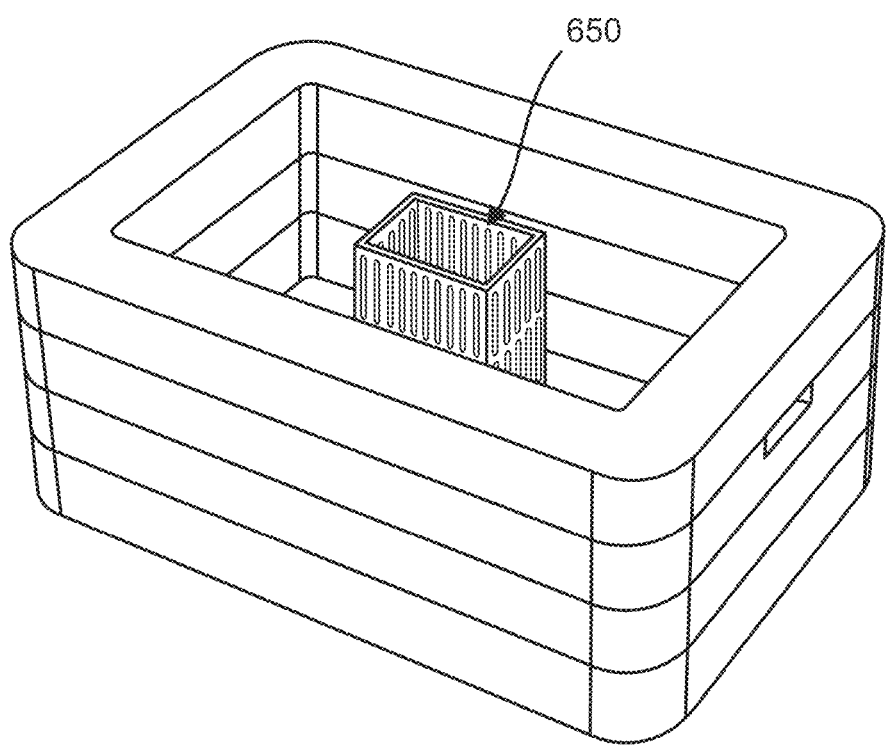
FIG. 19 shows a perspective view of the embodiment of FIG. 18

In a different embodiment shown in FIG. 18 and FIG. 19, the dry ice is not disposed at the periphery of the chamber against or near a chamber wall, but is instead retained in a dry ice retention space fashioned as a "free standing" column 650 (e.g., a cylindrical or rectangular column) in the central area of the chamber. In the example shown in FIG. 18, the width of the free standing column 650 is line bb-cc. In such embodiments, the retainer can be comprised entirely of a gas permeable retainer element or, alternatively, a portion can be gas impermeable. Referring to FIG. 1, it will be appreciated that a similar result occurs if the distance aa-aa' is large, rather than small as drawn.

FIG. 3 provides schematic cross-sections showing the relative orientations of (i) the chamber floor and wall(s), (ii) dry ice retainer elements, (iii) dry ice retention spaces containing dry ice pieces (cross-hatched), and (iv) the low temperature zone (heavy black line) of a variety of embodiments of the invention. It will be recognized that, in the figure, the height of the black line representing the low temperature zone is arbitrary. As discussed elsewhere herein, the low temperature zone extends, in various embodiments, one to ten inches, or more, above the chamber floor.

In some instances, the dimensions (capacity) of the dry ice retention space are selected to provide an optimized volume of dry ice for the overall volume of container. The chamber volume may be substantially larger than the volume of the dry ice retention space, or sum of the volumes of multiple retention spaces (for example, at least 5-fold larger, at least 6-fold larger, or at least 10-fold larger). The volume of the retention space(s) are generally less than 40% of the volume of the chamber, and often about 20% of the volume of the chamber, but may be smaller (e.g., 10-20%, 20%-30%, 25%-35%, 20%-40%, 25-40%, 30%-40%) or larger (e.g., 25%-50%, 30%-50%) of the volume of the chamber.

For example, in some instances the dimensions of the dry ice retainer space(s) are selected to achieve a "chamber volume" to "dry ice retention space" ratio of approximately 8:1, approximately 6:1, and in one embodiment a ratio of 4.5:1. In some instances the dimensions of the dry ice retention space(s) are selected to achieve a "chamber volume" to "dry ice retention space" (e.g., the total of the volumes of multiple dry ice retention spaces) greater than 4:1, greater than 4.5:1, greater than 6:1, greater than 8:1 or greater than 10:1. In other instances, the dimensions of dry ice retention space is selected to achieve a "working area volume" to "dry ice volume" ratio of approximately 7:1, approximately 5:1, and in one embodiment a ratio of 3.1:1.

Chamber volume is calculated as the volume of the chamber if it had a flat horizontal cover. For chambers having sides of different heights (see, e.g., FIG. 3K) the chamber volume is calculated as if all sides were the height of the shortest side. The volume of the dry ice retention space is calculated as the capacity of the dry ice holding portion of the retainer assuming no dead space (i.e., no unoccupied volume between dry ice pieces). It will be recognized that when dry ice pellets, for example, are used, the volume of the dry ice itself will be less than the capacity of the retention space, due to spaces between individual pellets.

Figure 6:
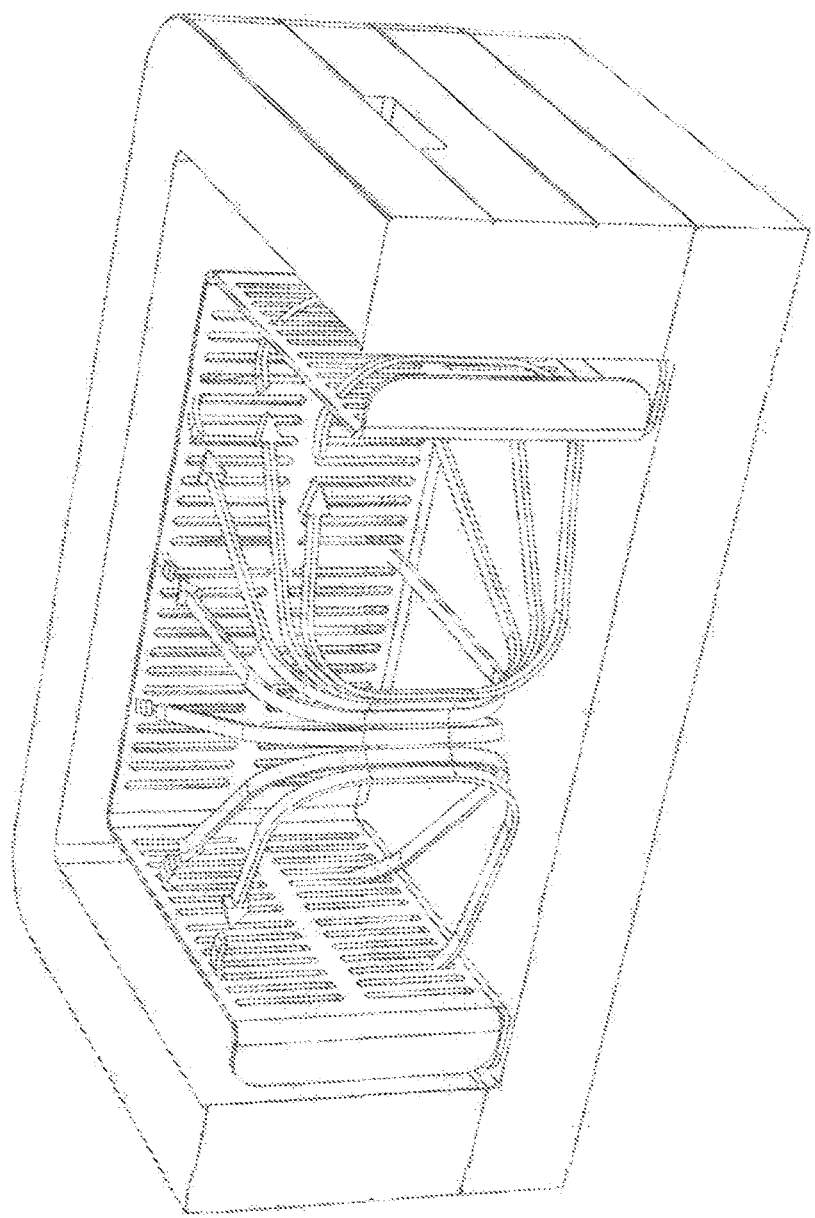
FIG. 6 illustrates a gas flow pattern during operation of an embodiment of the cryogenic system.

It will be appreciated that a wide variety of retainers are contemplated. Without intending to be bound by a particular mechanism, the retainer shown in FIG. 6 illustrates the operation of an embodiment of the invention. FIG. 6 illustrates an open-cavity work environment wherein continuous and extended operations may be performed at ultra-cold temperatures ranging from −50° C. to −78° C. While an open cavity of cold gas under static conditions will form a temperature gradient from the atmospheric temperature at the environmental interface to the coldest temperature at the cavity floor, the system comprises features that dynamically circulate the cavity gas past solid carbon dioxide refrigerant, thereby providing a lower and more uniform cavity temperature. This gas circulation feature provides an expanded region of low temperature in which temperature-sensitive operations may be safely conducted.

The internal cavity mixing process is based on cold convection. The cold $CO_2$ gas that is generated by sublimation of the dry ice ($CO_2$ solid) is denser than the slightly warmer gas inside the working cavity. As a result, the dense $CO_2$ gas will fall in a gravitational field toward the cavity floor. This motion creates a downward draft through the dry ice in the retainer to the cavity floor, then inward toward the center portion of the cavity. As the chamber has dry ice retainers on the rear and side walls of the cavity, the gas flow converges and upwells at the center front of the cavity. This gas flow pattern is readily visible during the initial cool-down (equilibration) phase of the run cycle when the gas motion is more vigorous due to the greater temperature differential between the −78° C. $CO_2$ gas produced by sublimation and the gas in the chamber. In addition, during the start-up phase any water vapor component in the atmospheric gas present inside the cavity will solidify forming a micro-crystal condensate that will allow the gas flow pattern to be observed. The gas flow pattern is depicted in the FIG. 6 graphic.

As the system approaches the steady working temperature, the cavity gas temperature is much closer to the $CO_2$ gas temperature at the solid $CO_2$ boundary, and as a result, the gas flow rate will slow, however the gas flow will persist in the same half-toroid pattern as long as there is environmental heat influx into the chamber. As the greatest thermal energy influx will occur at the atmospheric gas boundary layer near the top opening of the container, the uppermost region of the gas in the cavity will be warmer than the lower regions. The slow gas flow pattern will direct this warmer gas downward across the dry ice thereby cooling the gas to dry ice temperature, thereby maintaining the cooling cycle and gas flow pattern. In addition, as there is a continuous evolution of the $CO_2$ gas from the solid refrigerant, there will be a constant overflow of gas at the container rim. This feature has the effect of ejecting the warmest gas in the cavity in addition to sweeping away a portion of the atmospheric moisture condensate that forms at the environmental boundary thereby reducing the accumulation of solid precipitate on the dry ice and on the working cavity floor while maintaining visual clarity in the cavity field.

In addition to the temperature control, the release of $gCO_2$ to the chamber interior has the added advantage of enhancing visibility within the chamber. Atmospheric gas contains a percentage of water vapor that upon contact with a cold surface or gas will condense, and if in contact with sub-zero degree Celsius surface or gas will precipitate as a solid. On a surface with a temperature that is below zero degrees Celsius, a solid precipitate can be observed as a growing layer of frost. Over time the thickness of this frost layer of ice crystals can become extensive. In contact with a cold gas layer, however, the atmospheric moisture will precipitate as a fine crystal dust that will fall in a gravitational field and accumulate as an ice dust layer on surfaces below. This layer with time can accumulate depth and become problematic for many processes. In the instant invention, as the $sCO_2$ sublimates to gas, it expands approximately 770-fold, thereby creating a constant effluent of cold gas that overflows the container rim. The lateral motion of the gas at the surface serves to flush the crystalline water condensate over the container side before it has a chance to settle to the floor of the chamber, thereby significantly reducing both the suspended crystal density as well as the accumulation rate of the ice dust on the floor of the chamber. As the suspended ice crystals scatter light and present a visual impediment, a reduction in the suspended crystal density serves to greatly enhance visibility within the chamber.

D. Size and Shape of Dry Ice Pieces in Retainer; Delivery of Dry Ice to Retainer Space Dry ice pieces should be selected in accord with the needs of the operator and design of the retainer element. Dry ice pieces with a variety of shapes and dimensions can be obtained from commercial sources (e.g., Praxair, Danbury, Conn.) or prepared using well known methods. See, e.g., U.S. Pat. No. 5,475,981 (manufacture of dry ice pellets), and U.S. Pat. No. 2,608,838 (manufacture of dry ice spheres). For illustration and not limitation, common shapes and sizes include blocks (e.g., 10×10×11 inch, 50 lb blocks; 10×10×5 inch, 25 lb blocks), slices (e.g., 10×10×2 inch, 10 lb slices); cylindrical pellets (e.g., ⅖ inch diameter), "rice" pellets (e.g., ⅛" diameter); nuggets (e.g., ¼ inch, ⅝ inch and ¾ inch diameters by ¼ inch to 1.25 inch lengths).

Typically, forms that when loaded into the retainer form a high surface area network for gas flow (e.g., downward gas flow) are preferred for more efficient cooling, as discussed above. The size of the dry ice pieces is selected to maximize gas flow through the retention space and over the surface of the dry ice. Thus, very small pellets that may be packed together and impede gas flow, and large blocks which have less surface area and through which gas cannot flow are usually less desirable than dry ice pellets. Preferably, the dry ice pieces are selected so that in a fully filled retention space the dry ice occupies 40% to 80% of the volume, sometimes 50% to 70% of the volume, with the balance of the space being dead space.

In some embodiments, dry ice is delivered to the dry ice retention spaces manually, while in other embodiments, dry ice is introduced into the dry ice retention spaces by an automated delivery system. In some embodiments, dry ice pellets are delivered through a piping, hose, or gravity chute system. In some embodiments a microprocessor regulating the dry ice delivery is attached to a user touch screen interface. In some embodiments, the microprocessor regulating the dry ice delivery effects delivery in response to a signal from temperature sensor.

E. Low Temperature Zone

The cryogenic system may provide a low temperature zone temperature below a specified temperature (e.g., −50° C.) for at least a specified time (e.g., four hours) as measured at a defined distance (e.g., 1 inch) above the chamber floor in the sample-holding portion of the chamber after a equilibration period of specified time, e.g., less than two hours, without requiring the addition of more dry ice to the dry ice retention spaces, when the container is located within a 25° C. room with the top portion being constantly open for user access during said equilibration period and said at least four hours.

For a given operation, the upper boundary of the low temperature zone is at a specified height above the chamber floor below which the sustained temperature is less than a specified maximum. Typically, the maximum temperature is −50° C. and may be, for example −55° C., −60° C., or −65° C. Although the temperature at some height above the upper boundary may also be below the specified maximum, by limiting manipulation of samples to the low temperature zone, the operator, consumer, regulatory authorities, etc., may be confident the sample was maintained in the target temperature range. As discussed below, a temperature sensor and/or line laser (or other delineator) may be positioned at the upper boundary. In some embodiments the height of the upper boundary of the low temperature zone is predetermined for a particular system or configuration.

The height above the chamber floor of the upper boundary of the low temperature zone will depend on the configuration of the system. Generally, the boundary is significantly below the top (rim) of the chamber. In some embodiments of the invention, the boundary is above the chamber floor by about 50%, about 60%, about 70%, about 80%, or about 90% of the depth of the chamber. In some embodiments of the invention, the boundary is above the chamber floor by a distance equal to not more than 90%, more often not more than 75%, sometimes not more than 60%, sometimes not more than 50%, sometimes not more than 40%, and sometimes not more than 30% of the chamber depth. In some embodiments of the invention, the boundary is from 1 to 10 inches above the floor, such 1-3 inches, 2-5 inches, 3-6 inches, or 5-8 inches above the floor. In some embodiments of the invention, the boundary is about 1, about 1.5, about 2, about 2.5, about 3, about 3.5, about 4, about 4.5, about 5, about 5.5, about 6, about 6.5, about 7, about 7.5, about 10, about 10.5, or about 11 inches above the floor. In various embodiments the specified height at which the chamber temperature is measured is at least 1 inch, at least 2 inches, at least 3 inches, at least 4 inches, at least 5 inches, at least 6 inches, at least 7 inches, at least 8 inches, at least 9 inches, or at least 10 inches above the chamber floor.

In related embodiments, the system maintains the low temperature zone at a temperature below the specified temperature for at least four hours, at least six hours, at least eight hours, at least 10 hours, at least 12 hours, at least 15 hours, or at least 20 hours.

In some embodiments, the equilibration period is less than two hours, less than one hour or less than 30 minutes.

The present invention scalable, customizable and highly adaptable to a variety of applications and uses. Depending on the needs of the operator, the workstations may be made in various sizes and shapes, be equipped with robotics elements, be adapted for functional interaction with industry standard equipment, and the like.

Using the device and methods disclosed herein, samples can be maintained in a low temperature zone (less than −50° C.) for extended periods while allowing continuous operational access to the samples. The ordinarily skilled practitioner guided by this disclosure will recognize that several different factors contribute to the performance of the system (e.g., maintaining a temperature below a desired maximum, for a desired length of time, in a low temperature zone of having a desired volume). The ordinarily skilled practitioner guided by this disclosure will recognize that optimal performance requires consideration of various elements including: (1) the dry ice capacity of the dry ice retention spaces, and the volume of the dry ice retention spaces relative to the chamber volume, (2) the position and orientation of the retainers, (3) the size, shape and number of holes or openings in retainer element, (4) the size and shape of dry ice pieces loaded into the dry ice retention spaces, (5) the geometry of the chamber, (6) the materials used to construct the container or the insulative performance of the container and (7) the materials used to make the retainer or thermoconductivity of the retainer element).

Figure 8:
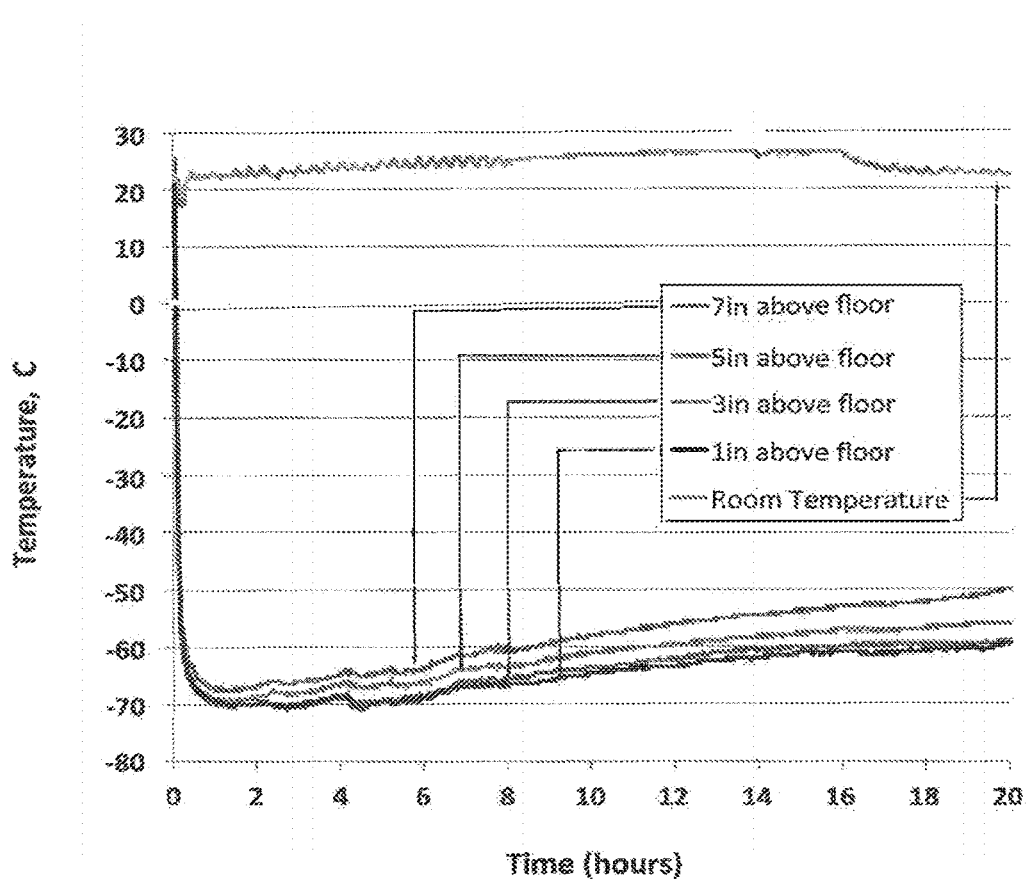
FIG. 8 shows generation of a −70° C. to −50° C. low temperature zone.

FIG. 8 illustrates that, by introducing dry ice into the dry ice retention space, a −78° C. to −50° C. low temperature zone can be generated in the working area portion of the chamber and maintained for several hours. The data in FIG. 8 were generated as follows:

A container with an internal chamber measurement of 27 inches length, 16 inches in width and 9.5 inches in depth, and insulated on the sides and underside by 2-inch thick expanded polystyrene (EPS) foam board was fitted with a retainer element with a height of 9 inches that was offset from the rear and side interior walls of container by a distance of 3 inches. A linear array of four thermocouple sensors was prepared in which the thermocouple sensors were spaced apart a distance of 2 inches. The linear array was fixed in a vertical orientation and placed inside the chamber at a central location such that the endmost sensor rested at a position 1 inch above the cavity floor. The thermocouple sensors were attached to a videographic data recorder and the system was activated to begin temperature recording. The volume between the retainer and interior wall was filled to a height level with the top of the retainer with pellets of dry ice measuring approximately 0.7 inches in diameter and 1 inch in length and the temperature data was recorded at 30 second intervals. Following a 2 hour interval, the dry ice was replenished to the original level and replenished again at two subsequent 2 hour intervals. After this time, the assembly was allowed to rest unattended for a total interval of about 13.5 hours. The temperature traces of the four thermocouples representing a height of 1, 3, 5, and 7 inches above the cavity floor are displayed in the figure.

F. Temperature Sensors

The workstations can be equipped with a variety of sensors, alarms, and means for collecting, storing, and transmitting signals. In some embodiments, the device comprises thermal sensors mounted at one or more locations in the chamber. Alarms may be used and configured to alert the user to an undesired temperature change or the need to add dry ice to the dry ice retention space. Recordings may be made of the temperature measurements taken, which may be transmitted to other devices.

In some embodiments, the chamber temperature is monitored by a single sensor, while in other embodiments, the chamber temperature is monitored by multiple sensors. Any thermal sensor that is accurate in the relevant temperature range (e.g., range −70° C. to −50° C. or range −78° C. to −50° C.) may be used in the present invention. Exemplary thermal sensors are thermocouple sensors and resistance temperature detectors (RTDs).

A temperature sensor may be positioned at the top (boundary) of the desired low temperature zone. Based on the determination of temperature at the specified point above the floor, it can be inferred that $CO_2$ gas temperature below that point will be between the monitored temperature and the dry ice sublimation temperature of −78° C. Generally, the temperature sensor of positioned significantly below the top (rim) of the chamber. In this context, "positioned" refers to the height above the chamber floor at which temperature is measured by the temperature sensor, for example the position of a temperature probe element. It will be appreciated that other, e.g., electronic, components of the sensor may be located elsewhere within or outside of the chamber.

In some embodiments of the invention, a temperature sensor is placed at a position that is from 1 to 10 inches above the floor, such 1-3 inches, 2-5 inches, 3-6 inches, or 5-8 inches above the floor. In some embodiments of the invention, a temperature sensor is positioned about 1, about 1.5, about 2, about 2.5, about 3, about 3.5, about 4, about 4.5, about 5, about 5.5, about 6, about 6.5, about 7, about 7.5, about 10, about 10.5, or about 11 inches above the floor. In some embodiments of the invention, a temperature sensor is placed at a position that is above the chamber floor by about 50%, about 60%, about 70%, about 80%, or about 90% of the depth of the chamber. For example, for a chamber depth of 48 inches, the sensor may be placed 24 inches (50%) above the floor. In some embodiments of the invention, a temperature sensor is placed at a position that is above the chamber floor by a distance equal to not more than 90%, more often not more than 75%, sometimes not more than 60%, sometimes not more than 50%, sometimes not more than 40%, and sometimes not more than 30% of the chamber depth.

A temperature sensor may be positioned in the chamber by any suitable means. The positioning mechanism may accommodate positioning at a fixed height, or may be adjustable. For illustration and not limitation, the sensor may be mounted on a chamber wall, may be directly or indirectly attached to a retainer, may be attached to a post projecting from the chamber floor, or may be suspended by wires. The sensor may be removably mounted (e.g., using magnets, Velcro, hooks, or other connectors) or permanently mounted. In some cases, the sensor is mounted on a sensor harness such as described below.

Figure 17:
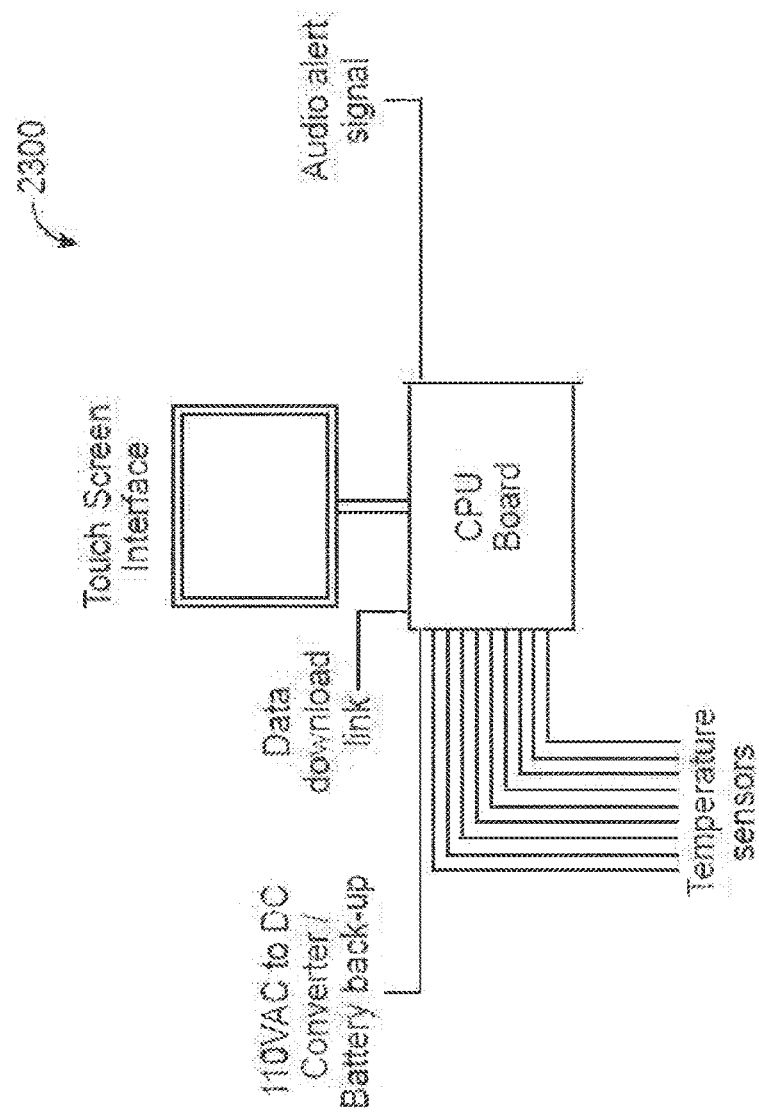
FIG. 17 shows an illustrative embodiment of signal linkages that can be received and sent from a system of the invention.

In some embodiments, an attached or remote microprocessor receives signal input from a temperature sensor. The microprocessor may be linked to the device through a hard-wired or wireless interface that sends sensor data back to the microprocessor. In some embodiments, the workstation receives control signals from the microprocessor. FIG. 17 shows an example of the signal linkages received and sent from an embodiment of the invention. In the schematic shown, the central microprocessor board receives input from eight separate temperature sensor and is linked to a battery system for uninterrupted power when the invention is detached from the AC line. The microprocessor board has a port for data download through hardwire or wireless linkage and a touch screen interface, while in other embodiments, the visual interface is an LCD screen and the user input takes place through other methods including but not limited to mechanical switches or capacitive switches. An audio output signal is linked to a transducer to alert an operator to various conditions or states which the invention may be in.

G. Sensor and/or Laser Harness

Some embodiments of the present invention further comprise a harness (or harnesses) as a means for supporting and suspending one or more components within the chamber at a desired height above the floor of the chamber. The harness may have a length approximately equal to the inner perimeter of the container's chamber, whereby the harness is positioned within the chamber and circumscribes the inner perimeter. In one embodiment the harness is rectangular with dimensions of about 47 inches by about 12.5 inches.

Components that may be supported by or attached to the harness include temperature sensors and lasers, as described below. Thus, harnesses may be referred to as a "sensor harness", a "laser harness", a "sensor and laser harness" and the like. It will be appreciated that, as apparent from context, one or more lasers may be attached to a "sensor harness", one or more sensors may be attached to a "laser harness", etc.

The harness may comprise a hollow tube having terminal ends in which are provided openings through which the hollow interior of harness may be accessed. In at least one embodiment, harness comprises a metallic material, such as stainless steel. A hollow interior of a harness provides a lumen through which lead wires may be ran to provide power to the various components supported on harness. Generally, the lead wires are fed through the openings in terminal ends.

Some instances of the present invention further comprise a sensor harness which comprises a wider diameter to permit easy passage of lead wires and other circuitry. Other instances provide an adjustable bracket for lowering harness deeper into the chamber, whereby to detect a colder zone within the container. Further still, some embodiments of the invention include a sensor harness comprising various cavities that allow individual sensors to be removed for calibration or cleaning.

In some embodiments, temperature sensors are provided on a sensor harness that is mounted to a retainer. FIG. 9 illustrates temperature sensors 2104, attached to sensor harness 2102, which is mounted to retainer 2140. Sensor harness 2102 may also be used with any of the other retainer devices disclosed herein. The sensor harness 2102 of the invention may generally comprise any size, shape and/or configuration that is compatible with the intended purposes disclosed herein. In some embodiments, sensor harness 2102 comprises a rigid, temperature resistant material, such as aluminum, stainless steel, or carbon fiber tubing.

Sensor harness 2102 of the present invention includes a rack 2106 comprising a tubular, conduit material having a hollow interior through which the temperature sensor lead wires and other circuitry may be routed and/or stored. In some instances, the temperature proper lead wires are routed to an outlet adapter 2112 through which the wires exit rack 2106 and container system 2100. In some instances, outlet adapter 2112 comprises an L-shaped, foam material that acts as a barrier to the leads and other circuitry that is located outside of rack 2106. The exposed portions of the lead wires may further be routed through a flexible nylon conduit (not shown) and the ends of the lead wires may be operatively coupled to a display unit, temperature meter, and/or other temperature sensing equipment, as discussed above.

Sensor harness 2102 generally comprises a shape that approximates the inner dimensions of retainer 2140 such that rack 2106 occupies the inner perimeter of retainer 2140. As thus configured, rack 2106 may be positioned within the interior of retainer 2140 with minimal effect on the available working space area of the container system.

In some instances, sensor harness 2102 further comprises a plurality of hangers 2120 configured to attach sensor harness 2102 to retainer 2140. Hangers 2120 may comprise any shape, size and/or configuration that is compatible with its intended use. For example, in one embodiment hangers 2120 comprise a J-hook configuration. Hangers 2120 may further comprise any compatible material. For example, in some embodiments hangers 2120 comprise a rigid, temperature-resistant material, such as stainless steel.

In one embodiment, hanger 2120 comprises a first end that is coupled to rack 2106 and a second end forming a hook that compatibly receives the rim or top surface of retainer 2140. In one embodiment, hangers 2120 comprise a length that suspends rack 2106 and temperature sensor 2104 at approximately 6 inches from the floor of the device. In other instances, rack 2106 is selectively coupled to hangers 2120 such that the relative position of rack 2106 on hangers 2120 may be selectively adjusted to set a desired distance between rack 2106 and the floor of the device. In other embodiments, retainer 2140 may comprise a plurality of slots or other features for receiving the hook portion of hanger 2120 at various heights on retainer 2140. Thus, a user may select a desired height for temperature sensors 2104. A detailed view of rack 2106 and hangers 2120 is shown in FIG. 9B.

Figure 9A:
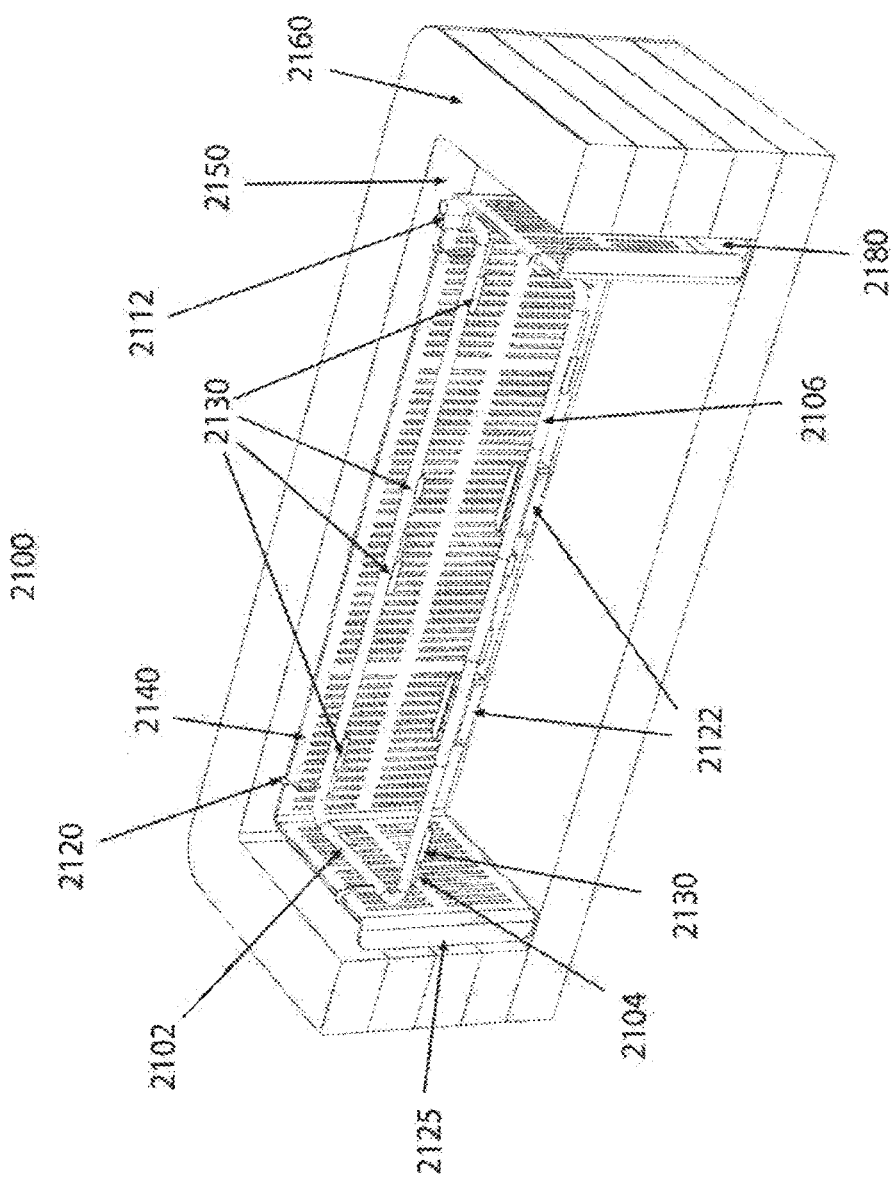
FIG. 9A shows a cross-section of a device similar to the device of FIG. 5, further comprising a harness, temperature sensor probes, and leveling lasers.
Figure 9B:
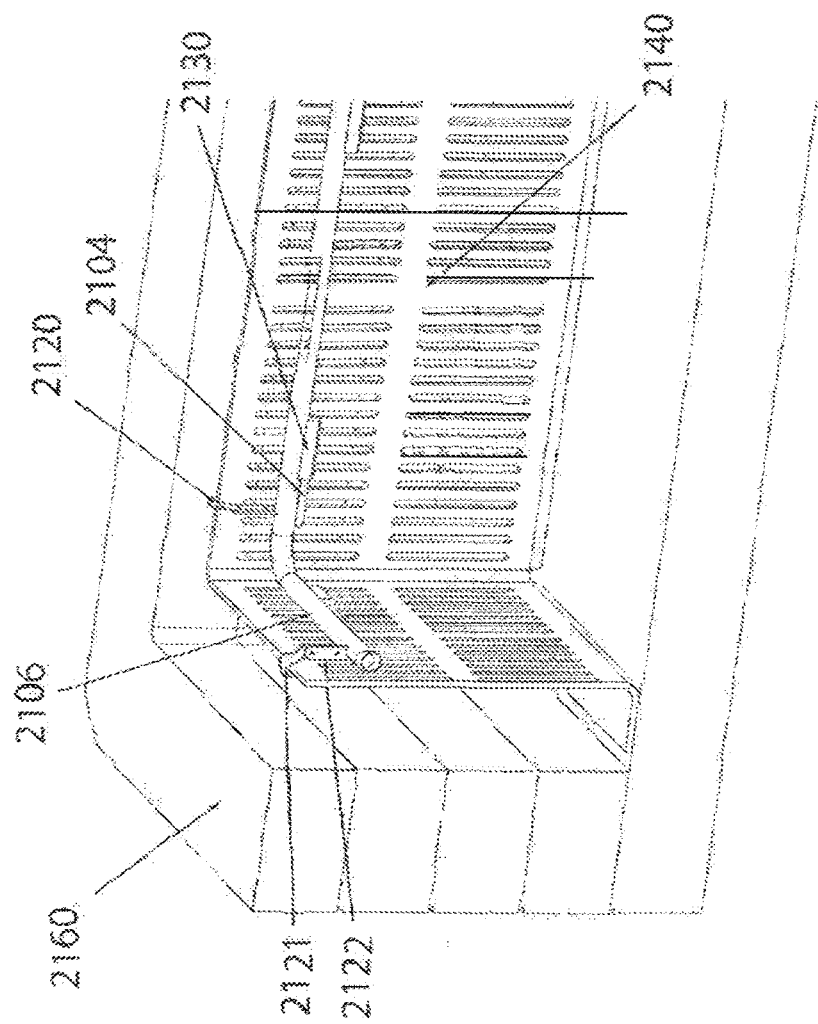
FIG. 9B shows a detailed view of a portion of FIG. 9A.

With continued reference to FIG. 9A and FIG. 9B, sensor harness 2102 may further comprise one or more temperature sensor adapters 2130 having a first aperture for receiving rack 2106, and a second aperture for receiving a temperature sensor 2104. Sensor adapter 2130 may comprise any length or dimension desired. In some instances, a pathway is provided between the first aperture and the second aperture, whereby the temperature sensor lead wired may pass from the second aperture and into the hollow interior of rack 2106 via the first aperture. Thus, the temperature sensor lead wire is completely concealed within sensor adapter 2130 and rack 2106. As is discussed in greater detail below, in addition to temperature sensors, other components, such as lasers, may be mounted on rack 2106.

Sensor adapter 2130 generally comprises a non-thermoconductive material, such as a cross-linked polyethylene foam, a urethane foam, a styrene foam, a polyvinyl foam, or a polymer blend foam. As such, temperature sensor 2104 is thermodynamically isolated from rack 2106, and may therefore accurately monitor the temperature of the working space without interference from the sensor harness 2102 material. In some instances, the position of sensor adapter 2130 is fixed via at least one of an interference fit or an adhesive. In other instances, the position of sensor adapter 2130 on rack 2106 may be adjusted by the user, as desired.

For accurate thermometric data collection from the temperature sensors, periodic calibration of the sensors will be required. The ability to rapidly disengage the sensor assembly (2104, 2106, 2120, 2130, 2102, 2122 in FIG. 9A) from the retainer (2140) and will allow the assembly to be placed into a temperature reference environment, such as a mechanical freezer, without detachment of the sensor leads from the temperature display/recorder/logger. The sensor adapter 2130 design generally allows for selective disengagement of the sensor from the adapter and selective extension of the sensor lead wire through the sensor harness to allow the sensors to be individually calibrated in a local reference temperature device such as a liquid bath.

In some instances, a harness comprises a plurality of slot openings on a bottom or under surface of the harness. The openings are configured to receive one or more temperature sensors. By placing openings on under surface, the temperature sensors are directed downwardly into the chamber, thereby optimizing their position for sensing the temperature within the chamber.

Openings generally comprise dimensions which ensure that the opening is entirely covered by a temperature sensor attached to the under surface of the harness. In one embodiment, the opening comprises a width of approximately 0.25 inches, and a length of approximately 0.75 inches.

Openings may be arranged on the under surface in any configuration that allows for accurate temperature measurement. In one embodiment, openings are evenly spaced along the length of harness. In another embodiment, openings are spaced about 8 inches to about 15 inches apart.

H. Lasers and Other Means for Low Temperature Zone Delineation

A detectable indicator of the boundary or upper limit of the low temperature zone is useful in the practice of the invention to ensure that sample is not moved out of the low temperature zone into upper regions of the container that may be outside the desired temperature range. A variety of methods may be used for such delineation including coloration (e.g., an indicator line printed on a chamber wall) or lights (e.g., embedded LED lights) positioned on the chamber wall at a specified height corresponding to the top of the low temperature. In one approach, the system may be equipped with lasers, for example as shown FIG. 9A and FIG. 9B, which project a linear guideline which indicates an upper, or maximum level of a controlled temperature working environment. Generally, the laser is suitable for projecting light along a horizontal path across the chamber at the level of the upper boundary of the low temperature zone.

In certain embodiments a "line laser" is used to delineate the upper boundary of the low temperature zone. Line lasers (sometimes referred to as "fan lasers") project a horizontal laser line ("laser leveling line" or "fan array"). In some embodiments a horizontal rotary laser is used. Lasers are commercially available from a variety of sources including Quarton Inc., 17700 Castleton St., City of Industry, CA 91748 (1 mW 650NM line laser part number VLM-650-27-LPA) and Johnson Level, 6333 W. Donges Bay Road I Mequon, Wis. 53092). In some embodiments a "self-leveling" laser is used.

Referring to FIG. 9A and FIG. 9B, in some instances, leveling lasers 2122 comprise a laser line filter that is configured to project a laser leveling line at one or more surfaces of retainer 2140 and/or container 2160. Leveling lasers 2122, are provided as a means of ensuring that container system 2100, retainer 2140 and sensor harness 2102 are level and remain level during use of the device. In one embodiment, a first leveling laser 2122 projects a laser leveling line in an x-axis, and a second leveling laser 2122 projects a laser leveling line in a y-axis. Leveling lasers 2122 may further comprise adjustable mirrors to facilitate fine tuning of the laser leveling lines.

A line laser may be positioned in the chamber by any suitable means, such as the methods described hereinabove for positioning temperature sensors. For example, Sensor harness 2102 may further comprise one or more leveling lasers 2122 that is coupled to rack 2106. In some instances, leveling lasers 2122 comprise power leads that are routed through the hollow interior of rack 2106, and which exit rack 2106 via outlet adapter 2112. In other instances, leveling lasers 2122 comprise onboard power circuits.

In one aspect the cryogenic system is characterized by a chamber containing a combination of at least one temperature sensor and at least one detectable indicator (e.g., laser projection of a linear guideline). In one aspect the cryogenic system is characterized by a chamber containing the combination of a temperature sensor and detectable indicator (e.g., a laser line projection) where the sensor and indicator are positioned at the same or essentially the same height above the chamber floor. As used herein, "essentially the same height" means the sensor and indicator are at the same height plus or minus 1 inch, or plus or minus 0.5 inches. The laser is suitable for projecting light along a horizontal path at the same level as (in the same plane as) the sensor. Preferably the laser light traverses the interior of the chamber such that an object in the chamber that extends into or is transported through the horizontal plane at the level of the sensor is illuminated by laser light.

In one embodiment, leveling laser 2122 comprises a single housing in which is housed two or more lasers. The laser housing is generally compact and comprises a minimum profile to prevent interference with the work area of the chamber. In some instances, the laser housing has a length of approximately 5 inches, a depth of approximately 1.5 inches, and a height of approximately 1.4 inches. In another embodiment, the two or more lasers are housed within the housing at an outward angle of approximately 30° from a central axis of the housing.

Some implementations of the present invention further include a removable laser carriage having a magnetic mounting system. The mounting system comprises compatible electrical terminals or contacts that deliver electrical current to the laser diodes when the laser carriage is coupled to the sensor harness. The mounting system includes a harness adapter that is permanently coupled to the harness. An opening is provided in the harness and electrical lead wires extend out of the opening and through the harness adapter. A mounting plate is further provided having electrical terminals that attach to the lead wires, observing the polarity of the lead wires. The mounting plate is attached to the harness adapter via a fastener. The electrical terminals of the mounting plate protrude outwardly on a side of the plate that is opposite the harness adapter. The laser carriage further comprises a recess for receiving the mounting plate. The recess includes additional electrical leads that are in alignment with the electrical leads of the mounting plate. The electrical contacts points further form two of three points of interface between the laser carriage and the mounting plate, the third point being the end of an adjustment screw protruding from the laser carriage. Through extension or retraction of the adjustment screw, the projection angle of the laser carriage can be controlled to allow proper alignment of the laser fan plane. In some instances, the mounting plate and recess further comprise complementary magnets, whereby the mounting plate is temporarily or selectively coupled to the recesses via a magnetic interface.

In one version, the laser carriage comprises two laser diodes. The electrical terminals of the laser carriage are operably connected to the laser diodes via electrical lead wires. When the mounting plate is coupled to, or set into the recess of the laser carriage, electrical current is delivered to the laser diodes via the interface between the electrical terminals and respective lead wires. When desired, the laser carriage may be simply removed from the harness by separating the magnetic connection between the mounting plate and the laser carriage. The fit between the mounting plate and the recess ensure proper, repeatable alignment of the laser diodes within the chamber of the container.

A harness may comprise one or more (e.g., a pair) of openings positioned on the inside surface of the harness, such that openings are adjacent the inside front wall of the container. The openings are configured to receive one or more laser carriages, wherein the laser carriages house one or more laser diodes capable of emitting a fan array to form a level line on at least one of the interior sidewalls and the interior back wall of the container. In one embodiment, openings are provided in harness such that the light emitted by the laser diodes is directed away from a user and into the interior chamber of the container. The openings generally comprise dimension which ensure that the opening is entirely covered by a laser carriage attached to the inside surface of the harness. In one embodiment, the opening comprises a width of approximately 0.375 inches, and a length of approximately 1.0 inch.

Openings may be arranged on inside surface in any configuration that achieves a continuous level line on the sidewall and back wall interior surfaces of the container. In one embodiment, openings are evenly spaced along the inside surface of harness.

Some embodiments of the present invention further comprise a laser module that may be easily attached and removed from harness. This feature permits harness to be removed and cleaned without exposing the laser module and circuitry to moisture. The feature further permits easy replacement or swapping of the laser modules for a new or different laser module. In some instances, it may be desirable to use the container without a laser module. Thus, some embodiments of the present invention comprise a laser module that may be selectively added to or removed from the sensor harness.

Figure 10:
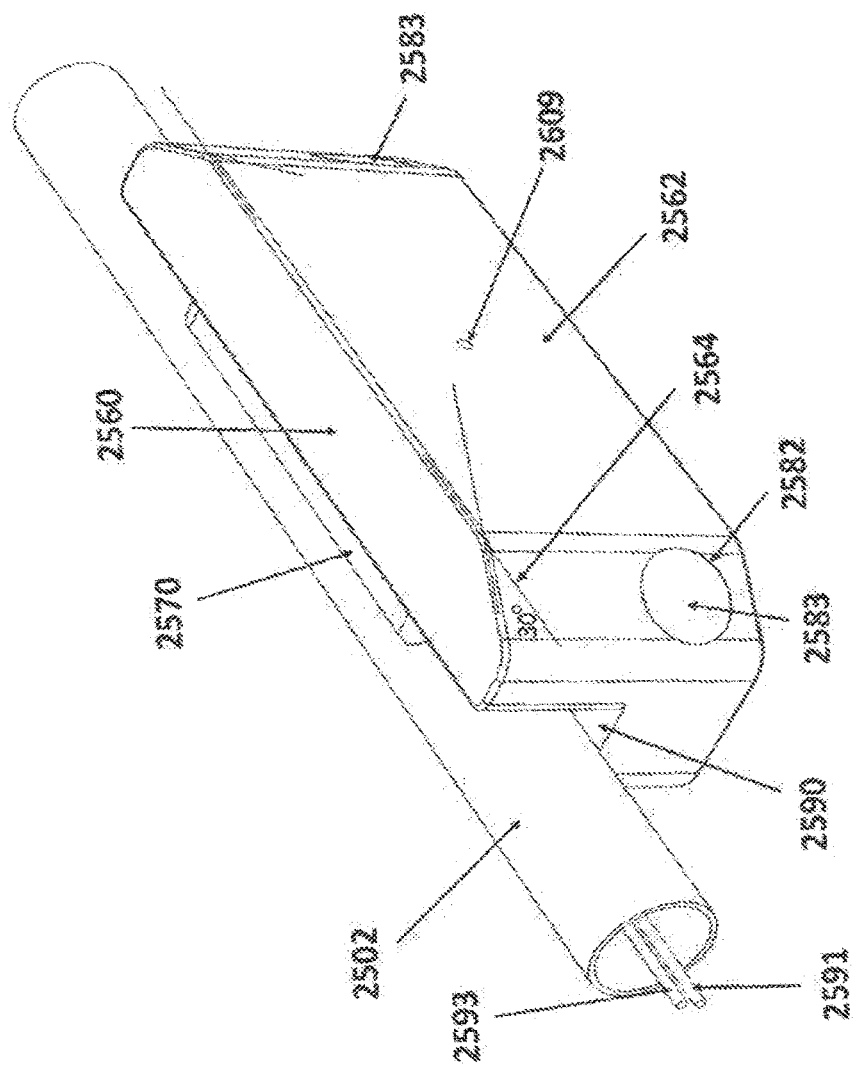
FIG. 10 provides a perspective view of a laser carriage selectively coupled to a harness via a mounting plate and harness adapter in accordance with a representative embodiment of the present invention.

FIG. 10 is a front perspective view of a laser carriage 2560 selectively coupled to harness 2502 via a harness adapter 2570. Laser carriage 2560 may comprise any size, shape, and general structure that are compatible with the features of the present invention. In one embodiment, laser carriage 2560 comprises a front surface 2562 in which is housed a pair of laser diodes 2583 which are capable of emitting a horizontal fan array to provide a level plane indicator. The laser diodes 2583 are deposited and housed in a compartment 2582 having an opening though which the laser is emitted. In some embodiments, the outer edges or corners of front surface 2562 are angled inwardly at approximately 30° with respect to the longitudinal axis 2564 of laser carriage 2560. Alternatively, in some instances front surface 2562 comprises a plane, and the corners or side edges of front surface 2562 are angled inwardly at approximately 30° with respect to the plane of front surface 2562. As such, the central axis of each compartment 2582 is angled outwardly at approximately 30° from the plane of front surface 2562. These angled surfaces, and the respective angled positions of laser diodes 2583, achieve a continuous level line emitted on the sidewall and back wall interior surfaces of the container.

In some instances, laser carriage 2560 comprises an L-shape, whereby a space 2590 is provided for accommodating placement of harness 2502. This L-shaped configuration further provides for placement of various components within the carriage housing. In other embodiments, laser carriage 2560 comprises another shape that is compatible with the intended use of laser carriage 2560.

Figure 11:
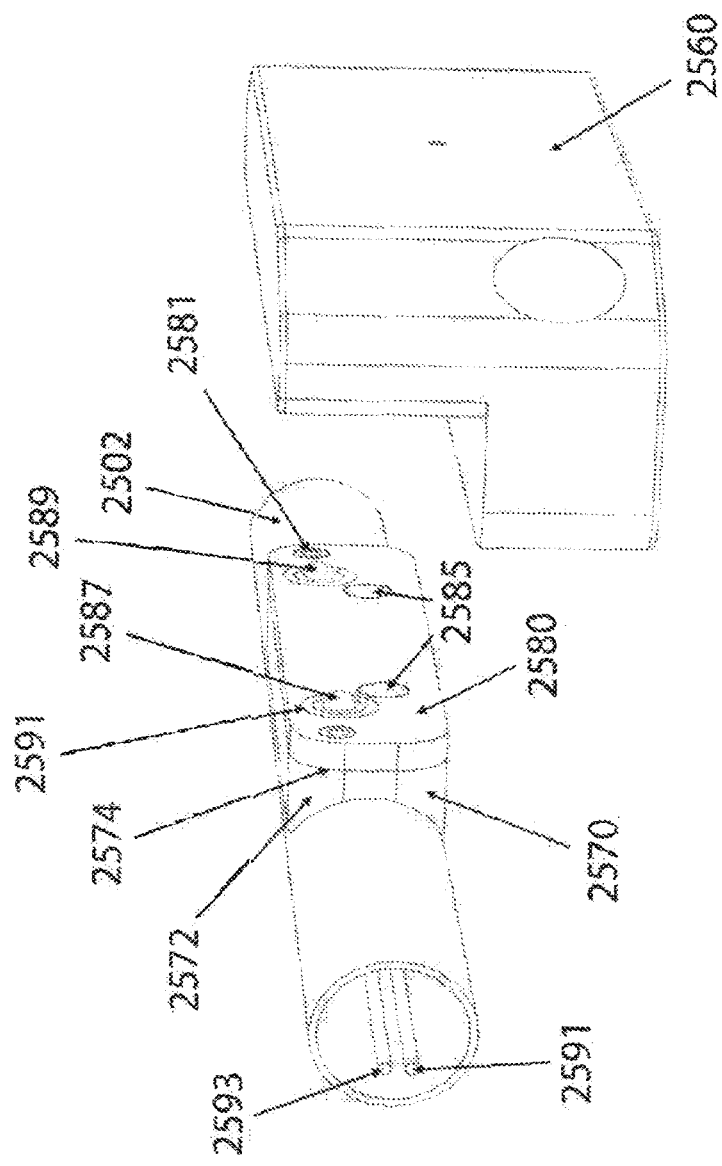
FIG. 11 provides a perspective view of a laser carriage detached from the harness, wherein the mounting plate and harness adapter remain coupled to the harness in accordance with a representative embodiment of the present invention.

Referring now to FIG. 11, laser carriage 2560 is shown separated from harness adapter 2570 and harness 2502. Harness adapter 2570 comprises a concave face 2572 configured to receive harness 2502. In some instances, harness adapter 2570 is permanently attached to harness 2502 over opening 2530 (see FIG. 12), such as by braising, welding, a temperature-resistant epoxy, or other compatible method. Harness adapter 2570 generally comprises a width that is greater than the width of opening 2530, whereby harness adapter 2570 completely surrounds and covers opening 2530.

Harness adapter 2570 further comprises a planar surface 2574 that is configured to receive carriage mounting plate 2580. Mounting plate 2580 is selectively attached to harness adapter 2570 by one or more fasteners 2581. In some instances, a fluid-tight interface is achieved between mounting plate 2580 and planer surface 2574 of harness adapter 2570.

Figure 12:
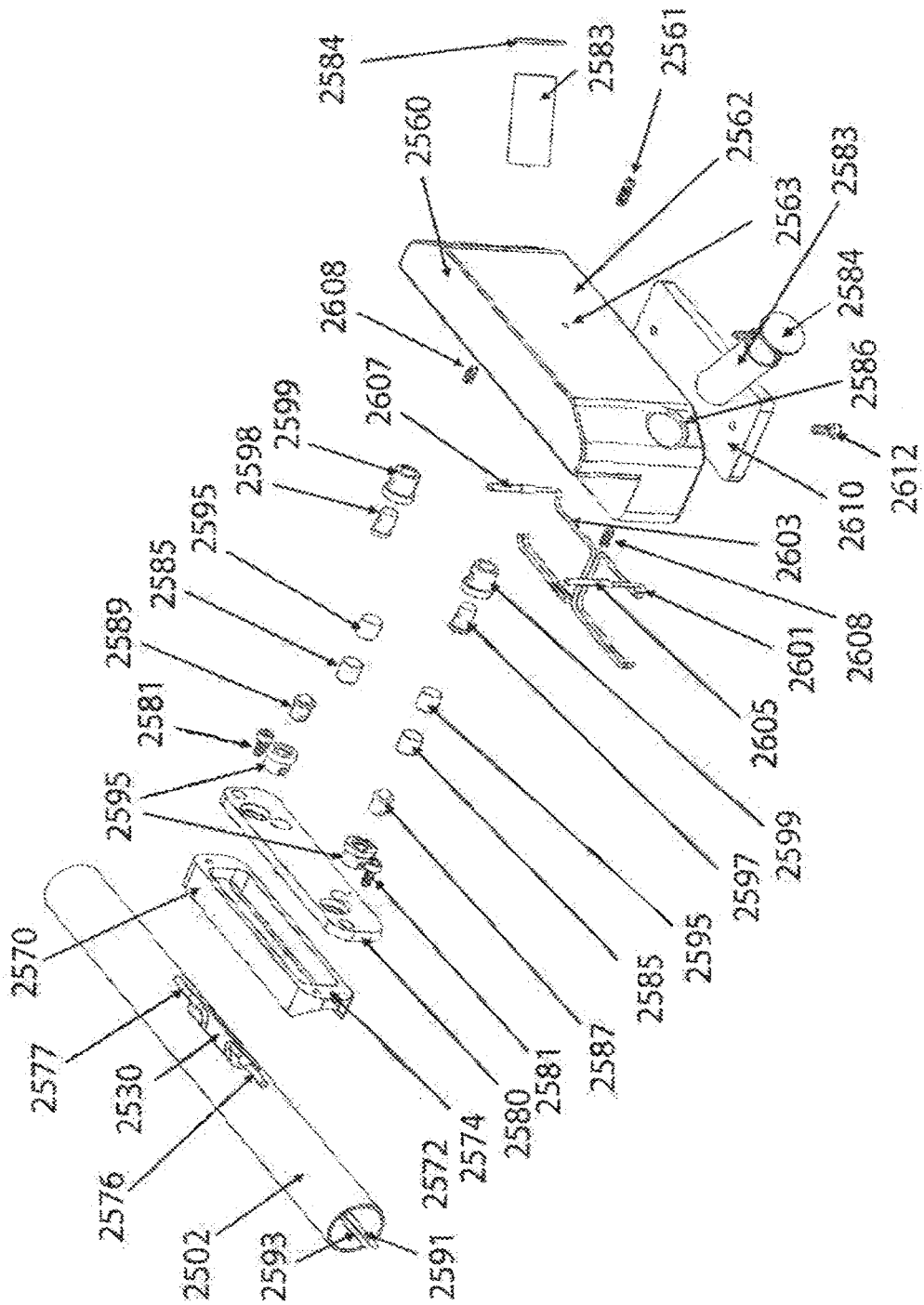
FIG. 12 provides an exploded view of a laser mounting system in accordance with a representative embodiment of the present invention.

Mounting plate 2580 further comprises mounting magnets 2585 that are embedded within mounting plate 2580 and flush with the plate's planar, front surface. Mounting magnets 2585 are positioned towards the outer edges of the plate's front surface at equal distances from a central vertical axis of the front surface. Mounting magnets 2585 are further positioned in alignment with corresponding magnets provided on laser carriage 2560, as shown in FIG. 12. Thus, laser carriage 2560 is selectively coupled to and removed from mounting plate 2580 via a magnetic interface.

Mounting plate 2580 further comprises a positive electrical terminal 2587 and a negative electrical terminal 2589 having a contact surface that extends outwardly from the plate's front surface. Each terminal is respectively coupled to positive 2591 and a negative lead wire which are fed through the hollow interior of harness 2502, as discussed above. In some embodiments, each terminal further comprises an insulator housing 2575 comprising a color or symbol to indicate the electrical polarity of the respective terminals. Electrical terminals 2587 and 2589 are securely seated into the insulated housings 2575 to insulate mounting plate 2570 from electrical current delivered to the respective electrical terminals.

Referring now to FIG. 12, an exploded view of the laser mounting assembly is shown. Harness adapter 2570 further comprises a hollow interior whereby to permit passage of lead wires 2591 and 2593 exiting from opening 2530. The electrical lead wires terminate in expanded pin jacks 2576 and 2577 for the positive wire and negative wire respectively. Mounting plate 2570 further comprises a plurality of openings, each configured to receive the insulator housings 2575, fasteners 2581, and mounting magnets 2585. Insulator housings 2575 further comprise an opening or lumen for receiving the positive and negative electrical terminals 2587 and 2589 respectively. Both the insulator housings 2575 and the electrical terminals 2587 and 2589 comprises a lateral hole recess through which the electrical wire expanded pin jacks 2576 and 2577 may be inserted to make an electrical connection by means of a friction fit. In some embodiments the electrical pin jacks are permanently secured to the electrical terminals 2587 and 2589 by means of the application of an epoxy or silicone adhesive, by solder joint, or by mechanical means such as a set screw (not shown).

Figure 14:
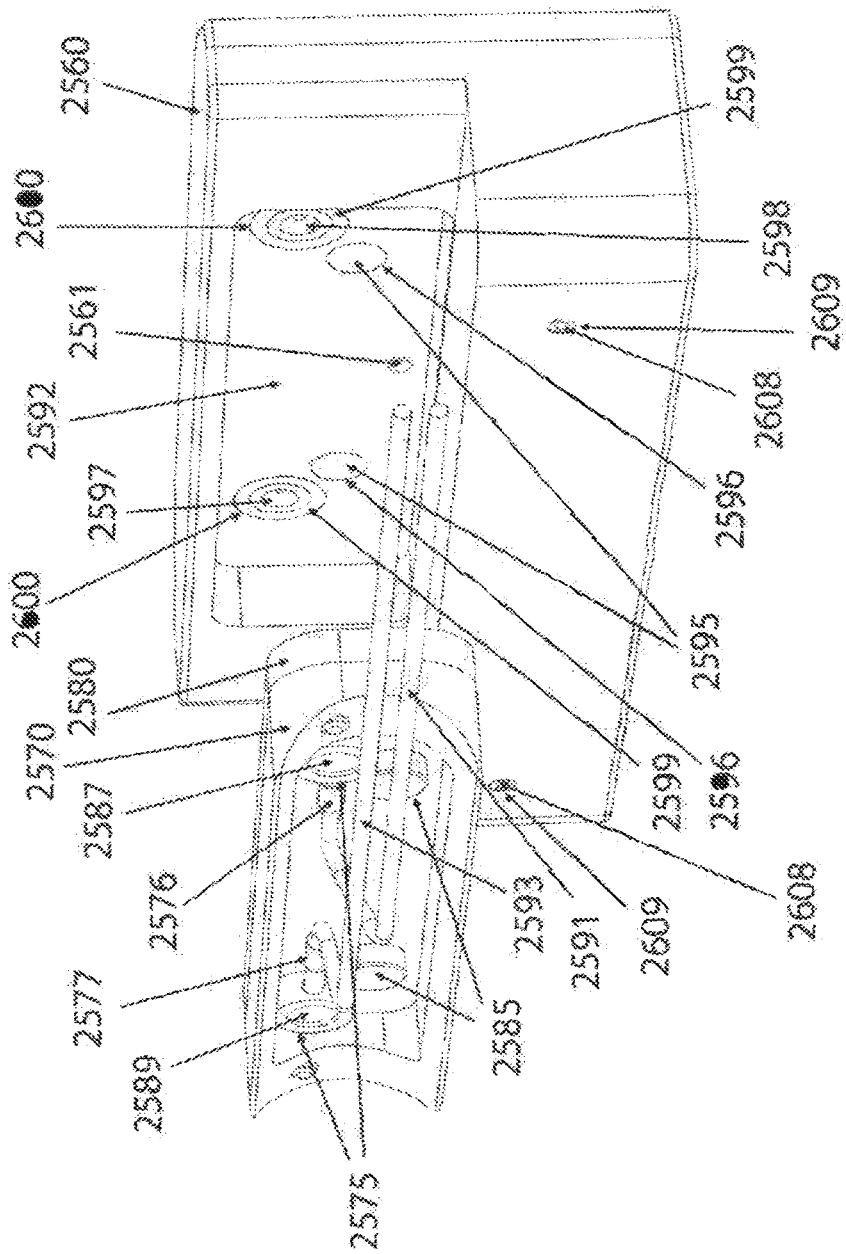
FIG. 14 is a detailed rear perspective view of a mounting plate and laser carriage in accordance with a representative embodiment of the present invention.

With continued reference to FIG. 12 and FIG. 14, laser carriage 2560 further comprises complementary mounting magnets 2595 that are inserted into respective openings 2596 (see FIG. 14) provided on the backside of laser carriage 2560. Laser carriage also comprises complementary electrical terminals 2597 (positive) and 2598 (negative) and insulator housings 2599 which are also inserted into openings 2600 in the laser carriage 2560. In some embodiments, electrical terminals 2587 and 2589 comprise a hemispherical surface that protrudes outwardly from the front surface of mounting plate 2580. Complementary electrical terminals 2597 comprise a concave surface that is configured to receive the hemispherical surface of terminals 2587. Thus, electrical current is passed from wire leads 2591 and 2593 to electrical terminals 2597 and 2589, respectively, via the interface between the hemispherical and concave surfaces. This interface surface further acts as a pivot point between mounting plate 2580 and laser carriage 2560, whereby laser carriage 2560 may be adjusted relative to mounting plate 2580 via a set screw 2561, without disrupting the electrical current, as described below. A positive branched wire set 2601 and a negative branched wire set 2603 are housed within the laser carriage 2560 and terminate in a positive expandable pin jack 2605 and a negative expandable pin jack 2607 respectively. The pin jacks engage the receiver holes of the positive electrical terminal 2597 and negative electrical terminal 2598. The branched wire sets are in contact with and supply power to the laser diode modules 2583 through permanent solder joint attachments, and are shown separated from the diodes in FIG. 12 for spatial clarity only. Laser carriage set screws 2608 are received by the threaded hole recesses 2609 for the purpose of securing the laser diode modules 2583 in position.

Figure 13:
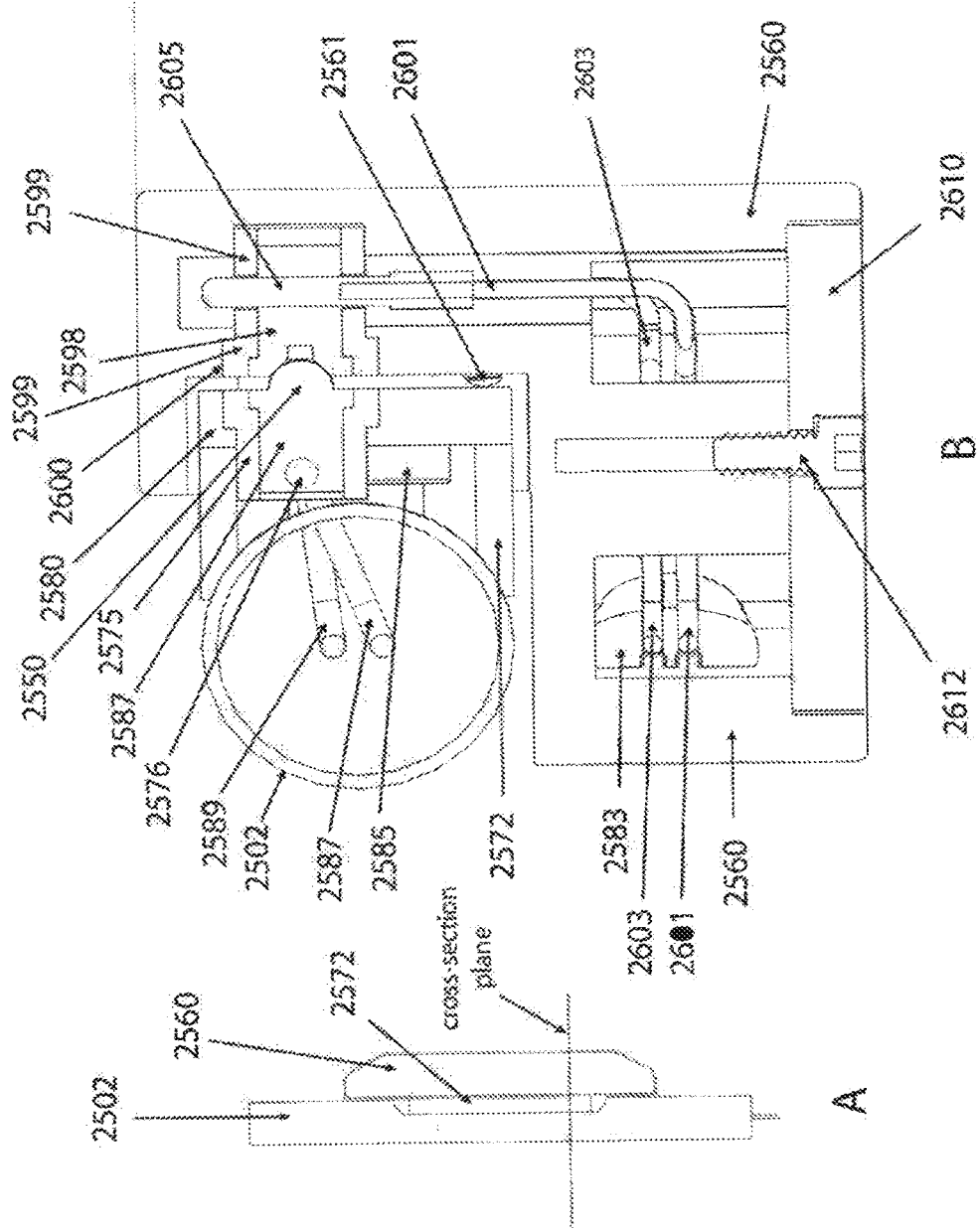
FIG. 13 is a cross-section view of a laser mounting system in accordance with a representative embodiment of the present invention.

With continued reference to FIG. 12 through FIG. 14, in some instances the backside surface of laser carriage 2560 comprises a recess 2592 having a length, width and depth that is slightly larger than the length, width and depth of mounting plate 2580. As such, a keyed connection is provided between mounting plate 2580 and laser carriage 2560, wherein mounting plate 2580 is configured to compatibly seat within recess 2592 when laser carriage is mounted on harness 2502 via mounting plate 2580 and harness adapter 2570. A magnetic interface between mounting magnet 2585 and complementary magnet 2595 provide a secure, yet temporary connection between mounting plate 2580 and laser carriage 2560. Laser carriage 2560 may further comprise a bottom plate 2610 that is secured to laser carriage 2560 by one or more fasteners 2612. Bottom plate 2610 may be removed to gain access to compartment 2582, lead wires 2601/2603, electrical terminals 2597, and laser diodes 2580. In some embodiments, the laser modules are covered by a glass cover plate 2584 that is fixed to the laser carriage cover glass recess 2586 my means of a silicone adhesive, thereby forming a water-proof seal.

Figure 15:
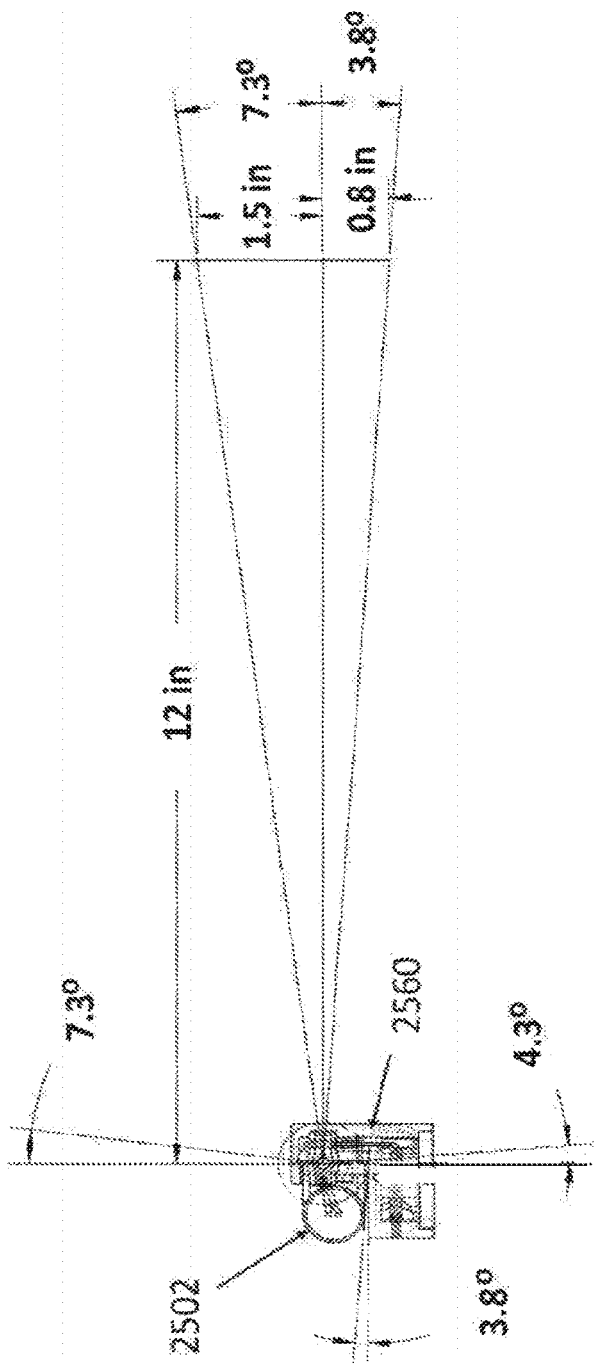
FIG. 15 is a cross-section view the laser carriage harness and adaptor showing the degree of pitch freedom of the laser carriage available by adjustment of the leveling screw, in accordance with a representative embodiment of the present invention.

In some embodiments, laser carriage 2560 further comprises a leveling set screw 2561 that engages the internal threads of hole 2563 through front surface 2562. Leveling set screw 2561 is generally centered between the positions of complementary magnets 2595 in a plane that is above or beneath a plane in which the respective central axes of the magnets 2595 are aligned. As such, the respective positions of magnets 2595 and set screw 2561 form a triangular plane within recess 2592. The triangular plane may be tilted, thereby adjusting the pitch of the fan arrays emitted by laser diodes 2580, by adjusting set screw 2561. The concave and convex interface surface between electrical terminals 2581 and 2597 permit tilting between mounting plate 2580 and recess 2592 without disrupting the electrical connection. The triangular configuration of magnets 2595 and set screw 2561 further permits exclusive adjustment of the pitch of the laser carriage 2560. Referring now to FIG. 15, in some instances, leveling set screw 2561 provides a laser beam projection incidence elevation adjustment of approximately 1.5 inches up, and 0.8 inches down at a horizontal distance of 12 inches from the pivot centers 2550, located within the mounting plate electrical contacts 2587 and 2589 (see also cross-section FIG. 13).

Figure 16:
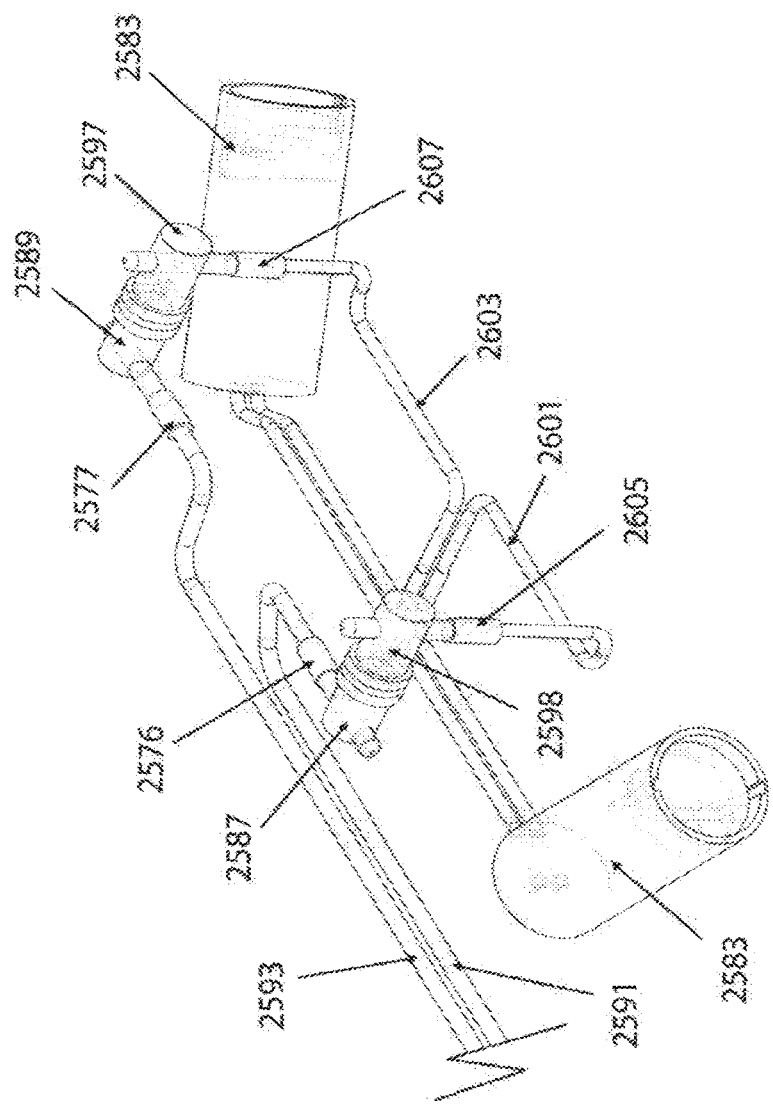
FIG. 16 is a three-dimensional perspective graphic showing the electrical pathway for the laser module power in accordance with a representative embodiment of the present invention.

Now referring to FIG. 16, isolated laser diode module 2583 poser circuit is shown. the Electrical lead wires 2591 and 2593 interface with the laser mount plate terminals 2587 and 2589 which in-turn are in contact with carriage terminals 2598 and 2587 respectively. The carriage jack pin contacts 2605 and 2607 are in contact with the carriage terminals 2598 and 2597 respectively. Positive electrical lead 2601 is joined to jack pin 2605 and negative electrical lead 2603 is joined to jack in 2607 and both electrical leads branch to supply the power to the laser diodes 2583 which are wired in parallel.

IV. Applications

The present invention is not limited by the type or nature of the sample or object placed into the device for maintenance at a desired temperature. For some applications, the device will be used to maintain a biological material in a container at a desired temperature range. For example, the biological material may be or comprise a nucleic acid (e.g. RNA or DNA or modified versions thereof), a protein (e.g. antibodies, chemokines, cytokines, enzymes, hormones, and lymphokines), a lipid (e.g. biological membranes), a virus (e.g. a vaccine), a cell (e.g. primary cell or stem cell or cell lines), bodily tissues and fluids (e.g. blood and blood products, including serum, biopsy materials), and foodstuffs. In various embodiments, the biological material is useful in the treatment or prevention of a disease; such biological materials include nucleic acid-based or protein-based drugs or vaccines. For example, certain envelope viruses useful as vaccines are exceptionally susceptible to degradation at higher temperatures, and the devices of the invention can be used to maintain them at temperatures that maximize stability.

For example, the environmentally controlled packaging systems of the present invention may be used for various processes, such as work-in-progress labeling of vials being transferred from freezers to a packaging line; transferring pre-conditioned packaging components (cartons and packaging inserts) from freezers to a packaging line; transferring finished drug product from a packing line to a freezer; and transferring labeled drug product vials into final product container within a −70° C. to −50° C. working environment of a packaging station.

For some applications, the device will be used to maintain an organic or inorganic compound in a container at a desired temperature range. For example, the organic compound can be a drug that is sensitive to temperature fluctuation, and illustrative inorganic materials include materials used in semiconductor chip manufacturing and aerospace engineering and catalysts.

Thus, the invention has wide application, including in the manufacturing, production and testing of aerospace materials, computers, cosmetics, drugs, food, semiconductors, advanced material research, and temperature-sensitive materials generally. The invention will find application in the labeling and packaging of temperature-sensitive materials such as biologics, cells used in stem cell and other therapies, cells used for the production of other products, compounds, drugs, enzymes, and vaccines. The invention will find application in the storage or performance of biological assays. The invention will find application in the transfer of biological and non-biological materials from one container to another, including automated transfers handled manually or by robotics. The invention will find application, without limitation, in biobanking, biorepository storage, cryogenic storage, and cryogenics. The invention will also find application in high-throughput screening, as in screens conducted for diagnostic purposes and drug discovery. The invention will also find application in welding of materials.

For certain applications, tools may be used to handle, manipulate, transfer, and package materials in an ultra-low temperature environment without the user being wholly exposed to those low temperatures. In one aspect of the invention, a vial picking hand tool is provided that is designed to permit a user to pick up and remove a single vial from a sample tray and transfer the vial to an empty product carton prepositioned in a product tray. The hand tool comprises long handles that allow the user to avoid inserting hands or arms into the ultra-cold working environment, thereby providing protection and comfort to the user.

A product carton closing hand tool is provided that is designed to permit a user to close the flaps and lid of a product carton after a product vial is inserted into the carton. The hand tool comprises long handles that allow the user to avoid inserting hands or arms into the ultra-cold working environment, thereby providing protection and comfort to the user.

V. Illustrative Embodiments

Below are provided various non-limiting Illustrative embodiments which illustrate the utility of some of the devices and embodiments of the present invention. In particular, the following Illustrative Embodiments illustrate various systems, methods and devices that provide an ultra-low temperature solution for packaging temperature-sensitive products and materials. Some embodiments of the instant invention ensure a working range of −70° C. to −50° C. which protects the integrity of the product, packaging, and personnel involved in the packaging process. Other embodiments comprise a plurality of individual modules that are combined together to provide an ultra-low temperature environment, wherein the combined modules comprise a complete product packaging operation which ensures user safety and comfort, as well as maximizes ease of product throughput and scalability. Further, in some embodiments a multiple-module packaging station is provided having one or more mobile modules, and one or more stationary modules, wherein the mobile and stationary modules comprise a complete product packaging operation. Those skilled in the art will recognize in view of this disclosure that any possible configuration or mobile and/or stationary devices can be deployed as needed, or desired, in accordance with the invention.

A. Illustrative Embodiment 1: Central Vial Transfer and Packaging Station

A central vial transfer and packaging station is provided which comprises a stationary system that provides a −78° C. to −50° C. work area for transferring finished product vials from a sample tray (for example, a 40-count sample tray or storage box) to a product carton (for example, a 20-count product tray or box). The station comprises a chamber made of cross-linked closed-cell HDPE foam and houses a dry ice retainer (DIR), sensors, lasers, and a device harness (i.e., a structure for supporting the sensors and lasers). The DIR is a retaining wall that holds the dry ice to the outer perimeter on three sides of the chamber and facilitates $CO_2$ gas flow throughout the chamber to create the −78° C. to −50° C. working environment within the chamber. Attached to the DIR is a device harness that is capable of supporting six Resistance Temperature Detectors (RTDs) (for example, Pyromation RTDs), four Channel Expansion Module sensors (CEMSs), and one or more lasers which provide guidelines designating the −78° C. to −50° C. work zone. In some instances, the RTDs are connected to a display and/or a computer system by a wire lead. In other instance, the RTDs are connected to a display and/or computer system by a wireless connection.

When the system power is set to the ON position, the RTDs begin real-time temperature monitoring and recording. When laser power is set to the ON position, the lasers project a fan pattern on a horizontal plane the marks the upper limit of the −78° C. to −50° C. zone. The projected laser light is invisible to the operator unless there is a reflection from an object that passes through the light plane. The reflected light provides a height indicator to the operator so that the operator can easily determine the upper boundary of the critical cold zone. The chamber is placed on a table at a working height (for example 40" from ground level to the top of the chamber). The chamber is filled with a predetermined amount of dry ice (for example, from approximately 200 to 250 pounds) and allowed to equilibrate to provide a −78° C. to −50° C. chamber working environment. In some instances, the equilibration process takes approximately one-half to one hour.

The chamber further includes a Videographic Recorder and Display (for example, an ABB ScreenMaster 1000 (SM1000)), and stack tower lights with audio and visual alarms to indicate a temperature fault. In some instances, solid state relays (SSRs) are controlled by digital signals sent from the Videographic Recorder and are used to activate higher voltage needed for the audible and visual alarms of the stack tower lights.

For portable units, the chamber further includes a battery box containing two 12V batteries 2460. In some instances, the battery box 2462 or enclosure is built according to NEMA 4× specifications. In one embodiment, a battery box 2462 is provided having a height of approximately 9.0 inches, a width of approximately 12.0 inches, and a depth of approximately 7.0 inches.

Portable units may further include a 24 VDC locking receptacle for recharging the batteries. For example, a 15 Amp, 125 volt, NEMA ML1P, 2P flanged inlet locking receptacle is provided which comprises a twist mini lock feature and is operably connected to the batteries 2460. The receptacle is rugged, resists impact, sunlight, chemicals and rough use. The battery charging cord further comprise a 24 VDC locking receptacle. In particular, the charging cord include a 15 Amp, 125 Volt, NEMA ML1R, 2P locking connector, mounted on the battery charger cord to provide a secure connection during battery charging operation. These receptacles are keyed to only accept NEMA ML1-C compatible plugs, thereby preventing incompatible charging systems.

Portable and/or non-portable units may additionally include a power supply and inverter for use with 120 and/or 220 volt receptacles. In some instances, 12V batteries or an AC receptacle power source is reduced to a 3.3 volt power source by means of a DC-DC or AC-DC converter, whereby the 3.3 volts is used to operate the laser.

The station may further include a front panel comprising a plurality of switches and other controls by which the station is operated. In some instances, the front panel is located above the Videographic Recorder. The front panel includes a system power switch which controls the "ON" and "OFF" status of the station. This switch is connected to the power source of the station to allow the user to selectively control and power all of the electrical components of the station, with the exception of the lasers. The front panel further comprises a laser power switch that is dedicated solely to the operation of the lasers. Thus, a user may selectively operate the station with or without the lasers.

The RTDs are attached to the device harness and are operably connected to the Videographic Recorder to monitor and record temperature changes inside the working zone. The low temperature zone height is marked by a spread-beam produced by the laser, wherein the spread-beam marks the low temperature zone boundary. The stack lights tower with audio and visual alarms provides the user with an audible and/or visual warning when the temperature within the chamber reaches a temperature limit set on the Videographic Recorder.

In some instances, a stack lights tower is provided having three operating levels, namely: 1) a green light zone which indicates that the operating conditions of the chamber are within a set specification; 2) a yellow light zone which indicates that the operating conditions of the chamber have deviated from a set specification; and 3) a red light zone which indicates that the operating conditions of the chamber are outside of an acceptable range based on a set specification, thereby requiring the user to take immediate action. Generally, the stack lights tower is coupled to an outer surface of the chamber, or a cart holding the chamber, such that the lights are clearly visible to the user. In some instances, the stack lights tower is mounted on the back of a cart that holds the chamber, wherein the tower is well within the view of the user.

It is generally preferred that a user wear cryogenic safety gloves to protect the user's arms and hands while working within the chamber. Thus, the user is protected from freezing burn injuries that may otherwise occur. Further, it is preferred that the user avoid contacting DIR, sensors, lasers, and device harness when dry ice is present in the chamber.

B. Illustrative Embodiment 2: Vial Transfer and Packaging Station

A representative embodiment of a mobile vial transfer and packaging station 2400 is shown in FIG. 2E. Mobile vial transfer and packaging station 2400 includes one or more mobile shuttles 2410, each mobile shuttle comprising a chamber 2420 that provides a −78° C. to −50° C. work area for transferring finished product vials from a sample tray to a product carton. Each mobile shuttle 2410 comprises a cart for transporting the mobile vial transfer and packaging station 2400 between desired locations.

The chamber 2420 of each mobile shuttle 2410 is made of a cross-linked, closed-cell HDPE foam and comprises an interior for receiving and housing a DIR, a plurality of sensors, one or more lasers, and a device harness. The DIR further comprises a plurality of vents or openings to facilitate passage of $CO_2$ gas through the DIR and into the work area of the chamber When the system power is set to an "ON" position, the sensors and RTDs begin real-time temperature monitoring and recording. When laser power is set to an "ON" position, the one or more lasers produce a linear guideline on the inner surface of the chamber which indicates the upper limit of the −78° C. to −50° C. environment or work zone. The chamber is further seated in a mobile stainless steel cart 2410 that is equipped with casters 2412, a swivel arm enclosure 2438 housing a display unit 2440 (for example, an ABB SM1000 display) and various switches 2446 and 2448 for system and laser power, a stack light alarm system 2450, and an electronic tag panel (e.g., available from AeroScout, Tel Aviv, Israel), not shown. In some instances, AeroScout probes are coupled to the device harness and operably connected to the AeroScout tags by a wire lead. AeroScout tags may alternatively be coupled to a panel 2452 on an exterior surface of the mobile stainless steel cart or display unit 2440, wherein the tags transmit wireless signals from the AeroScout probes to a central router and wireless system for recording.

The chamber 2420 of the mobile shuttle is equilibrated to a −78° C. to −50° C. temperature working environment by disposing from 200 to 250 pounds of dry ice into the volume or space interposed between the DIR and the inner wall surface of the chamber. The desired temperature working environment is attained in approximately one-half to one and one-half hours after the dry ice is added to the chamber.

Temperature changes within the work zone are monitored and recorded by the RTDs and an operably connected Videographic Recorder. The low temperature zone is marked by the spread-beam laser, thereby providing a visual indication of the working space boundary. The stack light tower 2450 further comprises audible and/or visual alarms which provide the user with an early warning when the temperature in the chamber reaches, or approaches a temperature limit set on the Videographic Recorder. The stack light tower 2450 may include various warning levels, as discussed in connection with Illustrative Embodiment 2, above.

The mobile shuttle 2410 enables a user to push or pull the vial transfer and packaging station 2400 to and from a desired location. In some instances, a mobile shuttle is used to transfer packaged materials from a room temperature location to a freezer location without removing the materials from the chamber or exposing the materials to an undesired temperature. In other instances, a mobile shuttle 2410 is used to transfer materials to or from a stationary or central vial transfer and packaging station.

C. Illustrative Embodiment 3: Multiple Module Transfer and Packaging Station A multiple module transfer and packaging station is provided which comprises a plurality of stationary vial transfer and packaging stations or modules that are interconnected to provide a single, complete product packaging operation. A multiple module transfer and packaging station is further provided which comprises a plurality of mobile vial transfer and packaging stations or modules that are interconnected to provide a single and mobile complete product packaging operation. Further still, a multiple module transfer and packaging station is provided which comprises a plurality of mobile and stationary vial transfer and packaging stations or modules that are either interconnected and/or used in concert to provide a single, complete product packaging operation. In some instances, a complete product packaging operation comprises four vial transfer and packaging stations.

Each of the chambers of the mobile and/or stationary modules has an opening defined by a rim. Generally, the rims of the module chambers are set at a uniform working height above the floor or ground on which the modules are supported. In some instances, the rims are set at a working height from approximately 28 inches to approximately 50 inches. In other instances, the rims are set at a working height from approximately 36 inches to approximately 44 inches. In one embodiment, the rims are set at a working height 2470 of approximately 40 inches.

The chambers are comprised of a highly durable HDPE foam material. The HDPE foam provides a highly insulative environment for the $CO_2$ gas to maintain a desired working temperature within the chamber. In some instances, the chamber comprises four sidewalls and a base which define the chamber. The sidewalls and base of the device comprises a wall thickness that provides sufficient insulation to prevent transfer of heat to the outer surface of the chamber. In some instances, the chamber comprises a wall thickness from approximately 2 inches to 8 inches. In other embodiments the chamber comprises a wall thickness of approximately 6 inches. Thus, the insulative properties of the HDPE foam, when provided at the desired wall thickness, optimally maintain a desired working temperature within the chamber, and prevent burn injuries to the user when the outer surface of the chamber is contacted.

D. Illustrative Embodiment 4: Chest Freezer Tower Rack Adaptor

A chest freezer tower rack adapter is provided that is designed to be placed on the floor of the chamber of a vial transfer and packaging station. The adapter may comprise a thermoconductive material, such as anodized aluminum, or an insulating material, such as HPDE foam, and includes a plurality of protrusions that are spaced to permit precise insertion of each protrusion into an individual opening in the back of a chest freezer rack when the chest freezer rack is laid horizontally on top of the rack adapter. The individual openings are located in the backsurface of the sample rack. The individual openings have a diameter or cross-section that permits easy insertion of the protrusions there through.

The rack adapter is placed on the floor of the chamber and permitted to equilibrate to the desired working temperature. A chest freezer rack is then placed over the rack adapter in a horizontal orientation such that the protrusions are lined up with, and inserted within the individual openings in the bottom of the sample rack. As the freezer rack descends over the rack adapter, the protrusions contact sample trays stored in the chest freezer rack, thereby lifting the sample trays out of their individual compartments and into an elevated position. The user may then easily access and grip the sample trays for easy transfer from the freezer rack to the chamber.

E. Illustrative Embodiment 5: Transfer and Packaging of Temperature-Sensitive Materials Process Flow and Set Up For set up, the user first checks that each module chamber contains a dry ice retainer (DIR). Dry ice is loaded into the area between the chamber wall and the DIR. Each module will require approximately 200-250 pounds of pelletized dry ice. The System Power switch is turned on, and the laser power switch, located above the ABB SM1000 Videographic Recorder display screen, is also turned on. The chamber is allowed to reach equilibrium temperature, which may take approximately one to one and one-half hours.

Product Flow

In a first product flow example, an operator takes a mobile shuttle equipped with a chest freezer tower rack adaptor to the freezer area, one chest freezer tower rack is placed onto the tower rack adaptor, and the rack is transported to the central packaging area and is positioned to the left of the central vial and transfer packaging station. An operator places stacks of 20-count product trays containing empty product cartons into another mobile shuttle and takes that to the central packaging area, also positioning it to the left of the central vial transfer and packaging station. A third mobile shuttle is positioned to the right of the central vial transfer and packaging station to receive finished product post-assembly in preparation for transportation to freezer storage.

Two operators work in front of the central vial transfer and packaging station to perform the vial transfer and carton closing procedure. A first operator transfers one 40-count tray containing frozen product vials from the mobile shuttle chest freezer tower rack to the central vial transfer and packaging station. A second operator transfers one 20-count product tray containing empty product cartons to the central vial transfer and packaging station. Using a hand-operated vial picking tool, and ensuring the vial stays below the laser guide lights, an operator transfers one vial to an empty product carton. This step is repeated until all empty cartons in the 20-count product tray are filled. Using a hand-operated carton-closing tool, the operator closes the flaps on each of the product cartons. When the 20-count product tray is filled with vials and all flaps are closed, the 20-count product tray is transferred to the empty chamber of the mobile shuttle positioned to the right of the central vial transfer and packaging station. An operator then transfers another 20-count product tray containing empty product cartons to the central vial transfer and packaging station. This process continues until all vials in all the 40-count sample trays in the mobile shuttle are transferred.

Figure 7:
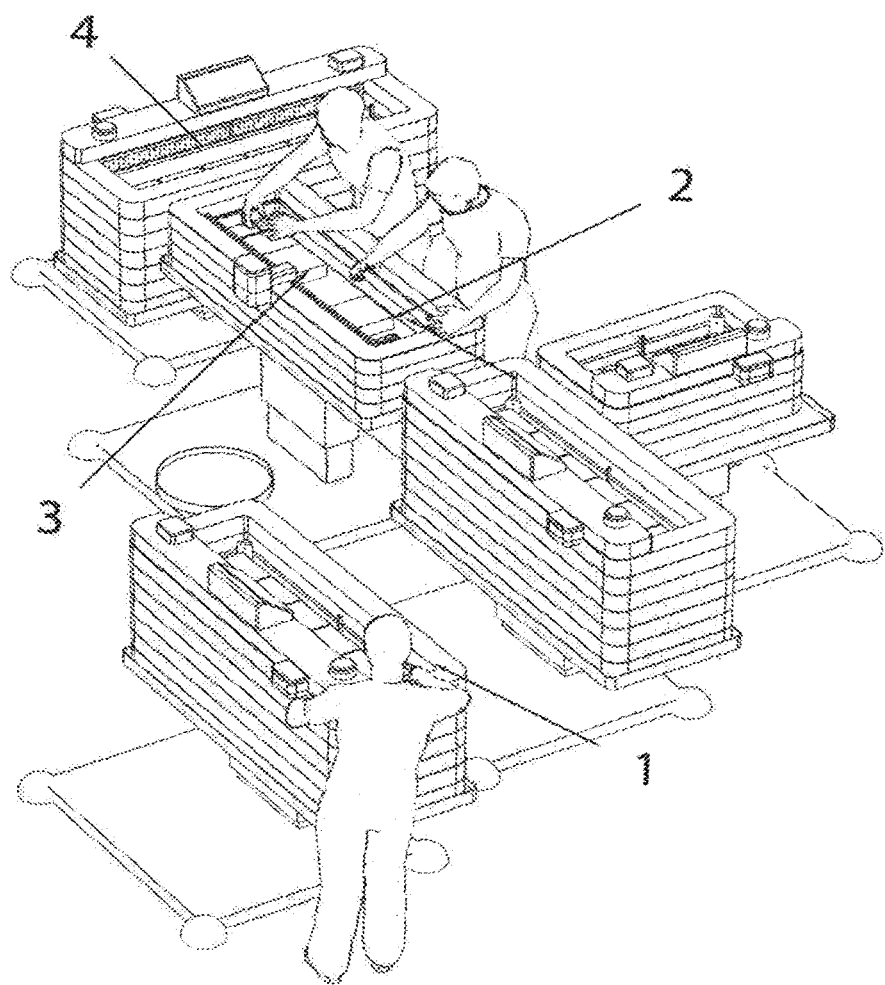
FIG. 7 shows a process flow layout using cryogenic devices.

In a second product flow example is illustrated in FIG. 7, which shows a series of the devices in an array for transferring vials into cartons and sealing the cartons. At station (1), carton trays are prechilled and container is moved to the transfer position. At station (2), cryobox and carton trays are moved to transfer container. At station (3) cartons are loaded with vials and passed to carton closing station. At station (4), loaded cartons are closed, then trays are laced into the buffer station. When full, trays are moved to freezer.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

I claim:
1. A system for cryogenic processing comprising:
   a container comprising a bottom, a first side, a second side, and a third side forming an interior chamber with an open top, the bottom having an interior floor surface, the first side having a first interior side surface, the second side having a second interior side surface, and the third side having a third interior side surface; and
   a perforated retainer including a first perforated portion, a second perforated portion, and at least one peripheral structure extending from at least one of the first perforated portion and the second perforated portion, the perforated retainer configured to be positioned in the interior chamber such that the first perforated portion is adjacent the first interior side surface and the second perforated portion is adjacent the second interior side surface to divide the interior chamber into a sample-holding portion and a dry ice retention space, and such that the at least one peripheral structure is adjacent the interior floor surface in the dry ice retention space, the sample-holding portion being between the first perforated portion and the second perforated portion, the dry ice retention space positioned on a first peripheral side and a second peripheral side of the sample-holding portion, perforations of the first perforated portion and the second perforated portion configured to exhaust gas directly into the interior chamber, wherein the system is configured to allow for access to the interior floor surface of the sample-holding portion while maintaining the sample-holding portion at an equilibrium condition at a temperature below an ambient temperature.

2. The system of claim 1 wherein, with the dry ice retention space filled with dry ice, the sample-holding portion of the interior chamber is maintained at a temperature below −50° C. for at least four hours as measured one inch above the interior floor surface, without requiring the addition of more dry ice to the dry ice retention space, when said container is located within a 25° C. room with the chamber opening being constantly open for user access during said four hours.

3. The system of claim 1 further comprising a cover configured to cover the open top of the interior chamber.

4. The system of claim 1 wherein the container is formed from modular components.

5. The system of claim 1 wherein the container comprises a material with a thermal conductivity less than 0.2 watts per meter kelvin.

6. The system of claim 1, wherein the perforated retainer includes a third perforated portion configured such that when the first perforated portion is adjacent the first interior side surface and the second perforated portion is adjacent the second interior side surface, then the third perforated portion is adjacent the third interior side surface and the dry ice retention space extends on a third peripheral side of the sample-holding portion.

7. The system of claim 1 wherein the perforated retainer is mounted to at least one of the first surface, the second interior side surface, and the third interior side surface.

8. The system of claim 1 wherein the dry ice retention space includes a free-standing column spaced from the first interior side surface, the second interior side surface, and the third interior side surface, such that dry ice put into the dry ice retention space is spaced from the first interior side surface, the second interior side surface, and the third interior side surface.

9. The system of claim 1 wherein the first perforated portion includes a perforated wall and the at least one peripheral structure extends from the perforated wall.

10. The system of claim 9 wherein the at least one peripheral structure includes a flange configured to extend between the perforated wall of the perforated retainer and the first interior side surface of the container, and to position the perforated wall of the perforated retainer relative to the first interior side surface of the container.

11. The system of claim 1 wherein the perforated retainer is constructed from aluminium and wherein perforations of the perforated retainer comprise slots that render the perforated retainer gas permeable.

12. The system of claim 1 wherein the perforated retainer is insertable and removable.

13. The system of claim 1 wherein the interior chamber is constructed to accept a plurality of different retainers with different properties.

14. The system of claim 1 wherein a volume of the interior chamber is at least six times the volume of the total volume of the dry ice retention space.

15. The system of claim 1, further comprising a temperature sensor in the interior chamber positioned at a height above the interior floor surface, wherein said sensor is suitable for measuring gas temperatures at least in the range −70° C. to −50° C.

16. The system of claim 1, further comprising multiple temperature sensors positioned above the interior floor surface.

17. The system of claim 16 further comprising a microprocessor configured to receive electric signals from one or more of the multiple temperature sensors, and configured to direct an electric signal to an alarm system as a result of a temperature in the sample-holding portion exceeding a preset limit.

18. The system of claim 15, further comprising a laser configured to project light along a horizontal path at the same level as the temperature sensor.

19. The system of claim 18 wherein the horizontal path marks an upper boundary of a low temperature zone.

20. The system of claim 1, further comprising a harness mounted on the perforated retainer, said harness having affixed thereto one or more temperature sensors or one of more laser diodes.

21. The system of claim 1 in which the dry ice retention space contains dry ice pieces and wherein the sample-holding portion of the chamber is substantially free of dry ice pieces.

22. A method of manipulating a sample under cryogenic conditions comprising manipulating the sample in the sample-holding portion of the system of claim 1.

* * * * *